(12) United States Patent
Takeshita et al.

(10) Patent No.: US 7,491,485 B2
(45) Date of Patent: Feb. 17, 2009

(54) RESIST COMPOSITION AND METHOD OF FORMING RESIST PATTERN

(75) Inventors: Masaru Takeshita, Kawasaki (JP); Komei Hirahara, Kawasaki (JP)

(73) Assignee: Tokyo Ohka Kogyo Co., Ltd., Kawasaki-shi (JP)

( * ) Notice: Subject to any disclaimer, the term of this patent is extended or adjusted under 35 U.S.C. 154(b) by 0 days.

(21) Appl. No.: 12/124,013

(22) Filed: May 20, 2008

(65) Prior Publication Data

US 2008/0292988 A1    Nov. 27, 2008

(30) Foreign Application Priority Data

May 23, 2007    (JP)    ............... 2007-136745

(51) Int. Cl.
*G03F 7/004* (2006.01)
*G03F 7/30* (2006.01)
(52) U.S. Cl. .................. 430/270.1; 430/326; 430/905; 430/910; 430/922
(58) Field of Classification Search ............. 430/270.1, 430/326, 905, 910, 922
See application file for complete search history.

(56) References Cited

U.S. PATENT DOCUMENTS

| | | | |
|---|---|---|---|
| 5,945,517 A | 8/1999 | Nitta et al. | |
| 6,180,313 B1 | 1/2001 | Yukawa et al. | |
| 7,074,543 B2 | 7/2006 | Iwai et al. | |
| 7,230,121 B2 * | 6/2007 | Norcini et al. | ................. 549/3 |
| 2007/0224540 A1 * | 9/2007 | Kamimura et al. | ....... 430/270.1 |

FOREIGN PATENT DOCUMENTS

| | | |
|---|---|---|
| JP | H09-208554 | 8/1997 |
| JP | H11-35551 | 2/1999 |
| JP | H11-35552 | 2/1999 |
| JP | H11-35573 | 2/1999 |
| JP | H11-322707 | 11/1999 |
| JP | 2003-241385 | 8/2003 |
| JP | 2005-37888 | 2/2005 |
| WO | WO 2004/074242 | 9/2004 |

* cited by examiner

*Primary Examiner*—John S Chu
(74) *Attorney, Agent, or Firm*—Knobbe, Martens, Olson & Bear, LLP

(57) ABSTRACT

This resist composition according to the present invention includes a base component (A) which exhibits changed solubility in an alkali developing solution under action of acid, and an acid generator component (B) which generates an acid upon exposure, wherein the acid generator component (B) includes an acid generator (B1) represented by a general formula (b1-6-1) shown below and an acid generator (B2) represented by a general formula (b1-6-2) shown below:

[Chemical Formula 1]

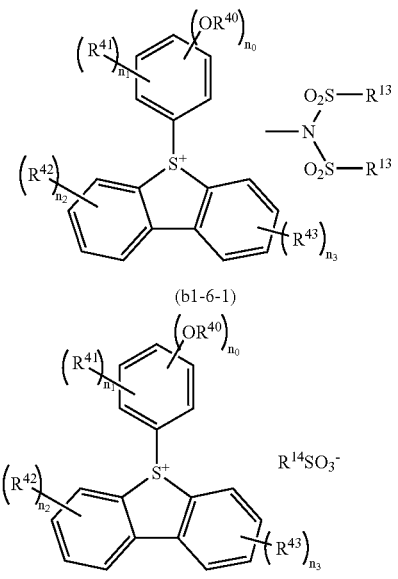

(wherein, $R^{40}$ represents a hydrogen atom or an alkyl group; $R^{41}$ represents a halogen atom, a halogenated alkyl group, an alkyl group, an acetyl group, a carboxyl group or a hydroxyalkyl group; $R^{42}$ and $R^{43}$ each independently represents a halogen atom, a halogenated alkyl group, an alkyl group, an acetyl group, an alkoxy group, a carboxyl group or a hydroxyalkyl group; $n_0$ to $n_3$ each independently represents an integer of 0 to 3, with the proviso that $n_0+n_1$ is 5 or less; $R^{13}$ each independently represents a linear or branched alkyl group of 1 to 10 carbon atoms in which at least one hydrogen atom is substituted with a fluorine atom, and two of $R^{13}$ may be bonded mutually to form a ring structure; $R^{14}$ represents a linear, branched or cyclic alkyl group, a linear, branched or cyclic halogenated alkyl group, an aryl group or an alkenyl group, which may contain a substituent group).

9 Claims, No Drawings

RESIST COMPOSITION AND METHOD OF FORMING RESIST PATTERN

RELATED APPLICATIONS

This application claims priority to Japanese Patent Application No. 2007-136745, filed May 23, 2007, the entire contents of which are incorporated herein by reference.

TECHNICAL FIELD

The present invention relates to a resist composition and a method of forming a resist pattern.

BACKGROUND ART

Lithography techniques include processes in which, for example, a resist film formed from a resist material is formed on top of a substrate, the resist film is selectively exposed with irradiation such as light, an electron beam or the like through a mask in which a predetermined pattern has been formed, and ten a developing treatment is conducted, thereby forming a resist pattern of the prescribed shape in the resist film. Resist materials in which the exposed portions change to become soluble in a developing liquid are termed positive materials, whereas resist materials in which the exposed portions change to become insoluble in the developing liquid are termed negative materials.

In recent years, in the production of semiconductor elements and liquid crystal display elements, advances in lithography techniques have led to rapid progress in the field of miniaturization.

Typically, these miniaturization techniques involve shortening the wavelength of the exposure light source. Conventionally, ultraviolet radiation typified by g-line and i-line radiation has been used, but nowadays KrF excimer lasers and ArF excimer lasers are starting to be introduced in mass production of semiconductor elements. Furthermore, research is also being conducted into lithography techniques that use $F_2$ excimer lasers, electron beams (EB), extreme ultraviolet radiation (EUV) and X-rays.

Resist materials are required to have lithography properties such as high sensitivity to the aforementioned light source and enough resolution to reproduce patterns with very fine dimensions. As resist materials which fulfill the aforementioned requirements, there is used a chemically-amplified resist containing a base resin that displays changed alkali solubility under action of acid, and an acid generator that generates acid upon exposure. For example, a chemically-amplified positive resist includes, as a base resin, a resin which exhibits increased alkali solubility in an alkali developing solution under action of an acid, and an acid generator. When an acid is generated from the acid generator upon exposure in the formation of a resist pattern, the exposed portions are converted to an alkali-soluble state.

Until recently, polyhydroxystyrene (PHS) or derivative resins (PHS-based resins) in which the hydroxyl groups have been protected with acid dissociable, dissolution inhibiting groups, which exhibit a high degree of transparency relative to KrF excimer laser (248 nm), have been used as the base resin of chemically-amplified resists. However, because PHS-based resins contain aromatic rings such as benzene rings, their transparency is inadequate for light with a wavelength shorter than 248 nm, such as light of 193 nm. Accordingly, chemically-amplified resists that use a PHS-based resin as the base resin have a disadvantage in that they have low resolution in processes that use, for example, light of 193 nm.

As a result, resins (acrylic resins) that contain structural units derived from (meth)acrylate esters within the main chain are now widely used as base resins for resists that use ArF excimer laser lithography, as they exhibit excellent transparency in the vicinity of 193 nm. In the case of a positive resist, as the base resin, those which have a structural unit derived from (meth)acrylate ester including an aliphatic polycyclic group-containing, tertiary alkyl ester-type acid dissociable, dissolution inhibiting group, such as a structural unit derived from 2-alkyl-2-adamantyl (meth)acrylate are mainly used (for example, see Patent Document 1).

Here, the term "(meth)acrylate ester" is a generic term that includes either or both of the acrylate ester having a hydrogen atom bonded with the a-position and the methacrylate ester having a methyl group bonded with the a-position. The term "(meth)acrylate" is a generic term that includes either or both of the acrylate having a hydrogen atom bonded with the a-position and the methacrylate having a methyl group bonded with the a-position. The term "(meth)acrylic acid" is a generic term that includes either or both of the acrylic acid having a hydrogen atom bonded with the a-position and the methacrylic acid having a methyl group bonded with the a-position.

On the other hand, as acid generators usable in a chemically-amplified resist, various types have been proposed including, for example, onium salt-based acid generators such as iodonium salts and sulfonium salts; oxime sulfonate-based acid generators; diazomethane-based acid generators; nitrobenzylsulfonate-based acid generators; iminosulfonate-based acid generators; and disulfone-based acid generators. Currently, as acid generators, those which include a triphenylsulfonium skeleton, dinaphthyl monophenylsulfonium skeleton, or the like are used (for example, see Patent Document 2).

[Patent Document 1]
Japanese Unexamined Patent Application, First Publication No. 2003-241385.

[Patent Document 2]
Japanese Unexamined Patent Application, First Publication No. 2005-37888.

DISCLOSURE OF THE INVENTION

Problems to be Solved by the Invention

In recent years, as requirements for high resolution increase with progress in the miniaturization of resist patterns, improvement in various lithography properties has been demanded. In particular, improvement of pattern shape is strongly desired. To satisfy the demands, the improvement of the verticality and rectangularity in a cross-sectional shape of a resist pattern is required by suppressing so-called footing on the interface between the resist pattern and substrate as well as the improvement of the reduction of roughness on the surface of a resist pattern and the reduction of line-edge roughness (LER; unevenness of the side wall of a resist pattern). It is considered that such an improvement of a pattern shape can be achieved by improving solubility of an acid generator in a resist solvent, transparency, dispersity in a resist film and the like.

The present invention takes the above circumstances into consideration, with an object of providing a resist composition which enables a pattern shape to be improved, and a method of forming a resist pattern using the resist composition.

Means for Solving the Problems

A first aspect of the present invention to solve the above problems is a resist composition, including a base component (A) which exhibits changed solubility in an alkali developing solution under action of acid, an acid-generator component (B) which generates acid upon exposure, wherein the acid-generator component (B) includes an acid generator (B1) represented by a general formula (b1-6-1) shown below and an acid generator (B2) represented by a general formula (b1-6-2) shown below:

[Chemical Formula 1]

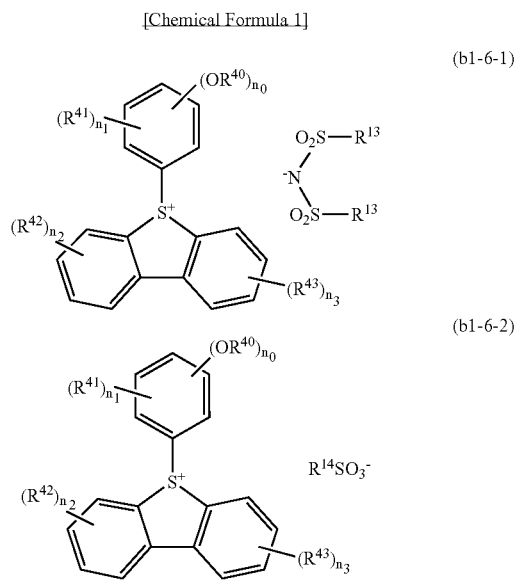

(wherein, $R^{40}$ represents a hydrogen atom or an alkyl group; $R^{41}$ represents a halogen atom, a halogenated alkyl group, an alkyl group, an acetyl group, a carboxyl group or a hydroxyalkyl group; $R^{42}$ and $R^{43}$ each independently represents a halogen atom, a halogenated alkyl group, an alkyl group, an acetyl group, an alkoxy group, a carboxyl group or a hydroxyalkyl group; $n_0$ to $n_3$ each independently represents an integer of 0 to 3, with the proviso that $n_0+n_1$ is 5 or less; $R^{13}$ each independently represents a linear or branched alkyl group of 1 to 10 carbon atoms in which at least one hydrogen atom is substituted with a fluorine atom, and two of $R^{13}$ may be bonded mutually to form a ring structure; $R^{14}$ represents a linear, branched or cyclic alkyl group, a linear, branched or cyclic halogenated alkyl group, an aryl group or an alkenyl group, which may contain a substituent group).

A second aspect of the present invention is a method of forming a resist pattern, which includes forming a resist film on a substrate using the resist composition described in the first aspect, exposing the resist film, and developing the resist film to form a resist pattern.

Here, the term "structural unit" represents a monomer unit that contributes to the formation of a resin component (polymer).

The term "exposure" is used as a general concept involving irradiation with any form of radiation.

The term "aliphatic cyclic group (alicyclic group)" means a monocyclic or polycyclic group which has no aromaticity.

The term "alkyl group" is a concept containing a linear, branched and cyclic monovalent saturated hydrocarbon group, unless another definition is particularly provided.

The term "lower alkyl group" represents an alkyl group of 1 to 5 carbon atoms. Similarly, the term "halogenated lower alkyl group" represents a halogenated alkyl group of 1 to 5 carbon atoms.

EFFECTS OF THE INVENTION

According to the present invention, there are provided a resist composition which enables pattern shape to be improved, and a method of forming a resist pattern using the resist composition.

BEST MODE FOR CARRYING OUT THE INVENTION

Hereinafter, the present invention will be described in more detail.

<<Resist Composition>>

A resist composition according to the first aspect of the present invention includes a base component (A) (hereinafter, referred to as component (A)) which exhibits changed solubility in an alkali developing solution under action of acid, and an acid-generator component (B) (hereinafter, referred to as component (B)) which generates an acid upon exposure, wherein the component (B) includes an acid generator (B1) represented by the general formula (b1-6-1) and an acid generator (B2) represented by the general formula (b1-6-2).

In the resist composition of the present invention, a polymer material which exhibits changed solubility in an alkali developing solution under action of acid can be preferably used as the component (A), and a low molecular material which exhibits changed solubility in an alkali developing solution under action of acid can also be used as the component (A).

Also, the resist composition of the present invention may be a negative resist composition or a positive resist composition.

In the case that the resist composition of the present invention is a negative resist composition, for example, the component (A) is an alkali-soluble resin, and a cross-linking agent (C) is blended with the resist composition.

In the negative resist composition, during resist pattern formation, when acid is generated from the component (B) upon exposure, the action of this acid causes cross-linking between the alkali-soluble resin and the cross-linking agent, and the cross-linked portion becomes alkali-insoluble.

As the alkali-soluble resin, it is preferable to use a resin having a structural unit derived from at least one of an a-(hydroxyalkyl)acrylic acid and a lower alkyl ester of a-(hydroxyalkyl)acrylic acid, because it enables formation of a satisfactory resist pattern with minimal swelling. Here, the term "a-(hydroxyalkyl)acrylic acid" represents one or both of an acrylic acid in which a hydrogen atom is bonded with the carbon atom at the a-position with which the carboxyl group bonded, and an a-hydroxyalkylacrylic acid in which a hydroxyalkyl group (preferably a hydroxyalkyl group of 1 to 5 carbon atoms) is bonded with the carbon atom at the a-position.

As the cross-linking agent (C), typically, an amino-based cross-linking agent such as a glycoluryl having a methylol group or alkoxymethyl group is preferable, as it enables formation of a satisfactory resist pattern with minimal swelling. The amount of the cross-linking agent (C) added is preferably within the range from 1 to 50 parts by weight, relative to 100 parts by weight of the alkali-soluble resin.

In the case that the resist composition of the present invention is a positive resist composition, the component (A) is insoluble in an alkali developing solution before exposure. When the acid generated from the component (B) upon exposure acts on the component (A), the acid dissociable, dissolution inhibiting groups are dissociated, and the solubility of the entire component (A) in the alkali developing solution is enhanced. As a result, the positive resist composition changes from an alkali-insoluble state to an alkali-soluble state. Therefore, in the formation of a resist pattern, when a resist film obtained by applying the positive resist composition on the substrate is subjected to selective exposure, the exposed area becomes soluble in an alkali, while the unexposed area remains alkali-insoluble, and hence a resist pattern can be formed by a developing treatment with an alkali.

In the resist composition of the present invention, the component (A) is preferably a base component which exhibits increased solubility in an alkali developing solution under action of acid. That is, the resist composition of the present invention is preferably a positive resist composition. Also, the component (A) is preferably a resin component (A1) (hereinafter, referred to as component (A1)) which increases alkali solubility under action of acid.

Component (A1)

The component (A1) suitably used in the positive resist composition preferably includes a structural unit (a1) derived from an acrylate ester having an acid dissociable, dissolution inhibiting group.

Further, the component (A1) preferably includes a structural unit (a2) derived from an acrylate ester having a lactone-containing cyclic group.

Furthermore, the component (A1) preferably includes a structural unit (a3) derived from an acrylate ester having a polar group-containing aliphatic hydrocarbon group.

Here, the term "structural unit derived from an acrylate ester" in the present specification and claims represents a structural unit formed by cleavage of the ethylenic double bond of an acrylate ester.

The term "acrylate ester" is a concept containing an acrylate ester in which a hydrogen atom is bonded with a carbon atom at the a-position, and an a-substituted acrylate ester in which a hydrogen atom bonded with a carbon atom at the a-position is substituted with another substituent group (an atom or group other than a hydrogen atom).

Examples of the substituent group include a lower alkyl group, and a halogenated lower alkyl group. The term "a-position (carbon atom at the a-position)" in a structural unit derived from an acrylate ester represents a carbon atom with which a carbonyl group is bonded, if not otherwise specified.

In the acrylate ester, specific examples of the lower alkyl group as the substituent group at the a-position include linear or branched lower alkyl groups such as a methyl group, an ethyl group, a propyl group, an isopropyl group, an n-butyl group, an isobutyl group, a tert-butyl group, a pentyl group, an isopentyl group, and a neopentyl group.

Specific examples of the halogenated lower alkyl group include groups in which a part of or all of the hydrogen atoms of the aforementioned "lower alkyl group for the substituent group at the a-position" are substituted with halogen atoms. Examples of halogen atoms include a fluorine atom, a chlorine atom, a bromine atom and an iodine atom, and of these, a fluorine atom is particularly preferable.

In the present invention, the group which is bonded with the a-position is preferably a hydrogen atom, a lower alkyl group or a halogenated lower alkyl group, more preferably a hydrogen atom, a lower alkyl group or a fluorinated lower alkyl group, and still more preferably a hydrogen atom or a methyl group, in terms of industrial availability.

Structural Unit (a1)

Structural unit (a1) is a structural unit derived from an acrylate ester having an acid dissociable, dissolution inhibiting group.

As the acid dissociable, dissolution inhibiting group in the structural unit (a1), any of the groups that have been proposed as acid dissociable, dissolution inhibiting groups for the base resins of chemically amplified resists can be used, provided the group has an alkali dissolution-inhibiting effect that renders the entire component (A1) alkali-insoluble prior to dissociation, and then following dissociation by action of acid, causes the entire component (A1) to change to an alkali-soluble state.

Generally, groups that form either a cyclic or chain-like tertiary alkyl ester with the carboxyl group of the (meth)acrylic acid, and acetal-type acid dissociable, dissolution inhibiting groups such as alkoxyalkyl groups are widely known. Here, the term "(meth)acrylate ester" is a generic term that includes either or both of the acrylate ester having a hydrogen atom bonded with the a-position and the methacrylate ester having a methyl group bonded with the a-position.

Here, the term "tertiary alkyl ester" represents a structure in which an ester is formed by substituting the hydrogen atom of a carboxyl group with a chain-like or cyclic alkyl group, and a tertiary carbon atom within the chain-like or cyclic alkyl group is bonded with the oxygen atom at the terminal of the carbonyloxy group (—C(O)—O—). In the tertiary alkyl ester, the bond of the oxygen atom with the tertiary carbon atom is cleaved by the action of an acid.

Here, the chain-like or cyclic alkyl group may contain a substituent group.

Hereafter, for the sake of simplicity, groups that exhibit acid dissociability as a result of the formation of a tertiary alkyl ester with a carboxyl group are referred to as "tertiary alkyl ester-type acid dissociable, dissolution inhibiting groups".

Examples of tertiary alkyl ester-type acid dissociable, dissolution inhibiting groups include aliphatic branched, acid dissociable, dissolution inhibiting groups and aliphatic cyclic group-containing acid dissociable, dissolution inhibiting groups.

Here, in the present claims and specification, the term "aliphatic" is a relative concept used in relation to the term "aromatic", and defines a group or compound or the like that contains no aromaticity.

The term "aliphatic branched" represents a branched structure having no aromaticity.

The "aliphatic branched, acid dissociable, dissolution inhibiting group" is not limited to groups (hydrocarbon groups) composed of carbon atoms and hydrogen atoms, and is preferably a hydrocarbon group.

Further, the "hydrocarbon group" may be either saturated or unsaturated, and is preferably saturated.

Examples of aliphatic branched, acid dissociable, dissolution inhibiting groups include tertiary alkyl groups of 4 to 8 carbon atoms, and specific examples include a tert-butyl group, a tert-pentyl group and a tert-heptyl group.

The term "aliphatic cyclic group (alicyclic group)" means a monocyclic or polycyclic group which has no aromaticity.

The "aliphatic cyclic group" within the structural unit (a1) may or may not have a substituent group. Examples of substituent groups include a lower alkyl group of 1 to 5 carbon atoms, a fluorine atom, a fluorinated lower alkyl group of 1 to 5 carbon atoms, and an oxygen atom (=O).

The basic ring of the "aliphatic cyclic group" exclusive of substituent groups is not limited to groups (hydrocarbon groups) composed of carbon atoms and hydrogen atoms, and is preferably a hydrocarbon group. Further, the "hydrocarbon group" may be either saturated or unsaturated, and is preferably saturated. The "aliphatic cyclic group" is preferably a polycyclic group.

Examples of the aliphatic cyclic groups include groups in which one or more hydrogen atoms have been removed from a monocycloalkane or a polycycloalkane such as a bicycloalkane, tricycloalkane or tetracycloalkane in which a lower alkyl group, a fluorine atom or a fluorinated lower alkyl group may or may not be included as a substituent group. Specific examples thereof include groups in which two hydrogen atoms have been removed from a monocycloalkane such as cyclopentane and cyclohexane, and a polycycloalkane such as adamantane, norbornane, isobornane, tricyclodecane, and tetracyclododecane.

As the aliphatic cyclic group-containing acid dissociable, dissolution inhibiting group, for example, a group which has a tertiary carbon atom on the ring structure of the cycloalkyl group can be mentioned. Specific examples thereof include 2-methyl-2-adamantyl group and a 2-ethyl-2-adamantyl group. Further, in the structural units represented by general formulae (a1''-1) to (a1''-6) shown below, groups bonded with the oxygen atom of the carbonyloxy group (—C(O)—O—), that is, groups having an aliphatic cyclic group such as an adamantyl group, cyclohexyl group, cyclopentyl group, norbornyl group, tricyclodecanyl group or tetracyclodecanyl group, and a branched alkylene group having a tertiary carbon atom bonded thereto, can be exemplified.

[Chemical Formula 2]

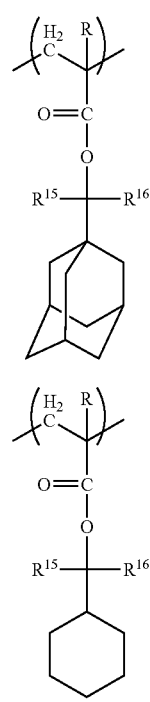

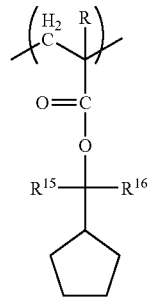

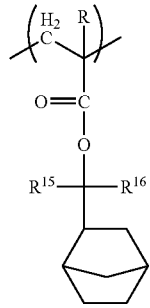

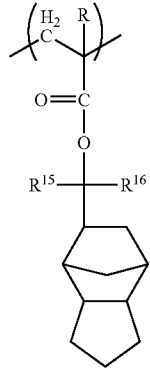

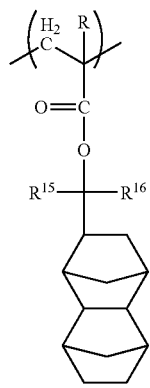

(wherein, R represents a hydrogen atom, a lower alkyl group or a halogenated lower alkyl group; and $R^{15}$ and $R^{16}$ each independently represents an alkyl group (may be linear or cyclic, and preferably an alkyl group of 1 to 5 carbon atoms).)

In the general formulae (a1''-1) to (a1''-6), the lower alkyl group or halogenated lower alkyl group for R are the same as the lower alkyl group or halogenated lower alkyl group which can be bonded with the α-position of the aforementioned acrylate ester.

An "acetal-type acid dissociable, dissolution inhibiting group" is generally substituted with a hydrogen atom at the terminal of an alkali-soluble group such as a carboxy group or a hydroxyl group, so as to be bonded with an oxygen atom. When acid is generated upon exposure, the generated acid acts to break the bond between the acetal-type acid dissociable, dissolution inhibiting group and the oxygen atom with which the acetal-type, acid dissociable, dissolution inhibiting group is bonded.

Examples of acetal-type acid dissociable, dissolution inhibiting groups include groups represented by a general formula (p1) shown below.

[Chemical Formula 3]

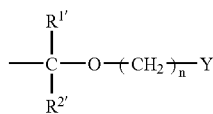

(p1)

(wherein, $R^{1'}$ and $R^{2'}$ each independently represents a hydrogen atom or a lower alkyl group; n represents an integer of 0 to 3; and Y represents a lower alkyl group or an aliphatic cyclic group.)

In the above formula, n is preferably an integer of 0 to 2, more preferably 0 or 1, and most preferably 0.

The lower alkyl group of $R^{1'}$ and $R^{2'}$ is the same as the lower allyl groups described above in R. As the lower alkyl group of $R^{1'}$ and $R^{2'}$, a methyl group or an ethyl group is preferable, and a methyl group is most preferable.

In the present invention, at least one of $R^{1'}$ and $R^{2'}$ is preferably a hydrogen atom. That is, it is preferable that the acid dissociable, dissolution inhibiting group (p1) be a group represented by a general formula (p1-1) shown below.

[Chemical Formula 4]

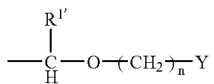

(p1-1)

(wherein, $R^{1'}$, n and Y represent the same as those described above.)

The lower alkyl group of Y represents the same as the lower alkyl group described above in R.

As the aliphatic cyclic group for Y, any of the aliphatic monocyclic or polycyclic groups which have been proposed for conventional ArF resists and the like can be used by being appropriately selected from those. For example, the same groups described above in the "aliphatic cyclic group" can be exemplified.

Further, as the acetal-type, acid dissociable, dissolution inhibiting group, groups represented by general formula (p2) shown below can also be exemplified.

[Chemical Formula 5]

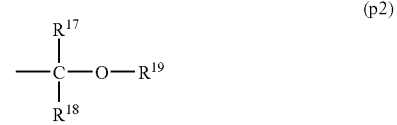

(p2)

(wherein $R^{17}$ and $R^{18}$ each independently represents a linear or branched alkyl group or a hydrogen atom; and $R^{19}$ represents a linear, branched or cyclic alkyl group. Alternately, $R^{17}$ and $R^{19}$ each independently represents a linear or branched alkylene group, wherein the terminal of $R^{17}$ may be bonded with the terminal of $R^{19}$ thereby forming a ring.)

The alkyl group for $R^{17}$ and $R^{18}$ preferably has 1 to 15 carbon atoms, and may be either linear or branched. As the alkyl group, an ethyl group or a methyl group is preferable, and a methyl group is most preferable.

It is particularly preferable that either one of $R^{17}$ and $R^{18}$ be a hydrogen atom, and the other be a methyl group.

$R^{19}$ represents a linear, branched or cyclic alkyl group which preferably has 1 to 15 carbon atoms, and may be any of linear, branched or cyclic.

When $R^{19}$ represents a linear or branched alkyl group, it is preferably an alkyl group of 1 to 5 carbon atoms, more preferably an ethyl group or methyl group, and most preferably an ethyl group.

When $R^{19}$ represents a cyclic alkyl group, it preferably has 4 to 15 carbon atoms, more preferably 4 to 12 carbon atoms, and most preferably 5 to 10 carbon atoms. Specific examples of the cyclic alkyl group include groups in which one or more hydrogen atoms have been removed from a monocycloalkane or a polycycloalkane such as a bicycloalkane, tricycloalkane or tetracycloalkane, in which a fluorine atom or a fluorinated alkyl group may or may not be included as a substituent group. Specific examples thereof include groups in which one or more hydrogen atoms have been removed from a monocycloalkane such as cyclopentane and cyclohexane, and a polycycloalkane such as adamantane, norbornane, isobornane, tricyclodecane, and tetracyclododecane. Of these, a group in which one or more hydrogen atoms have been removed from adamantane is preferable.

In the general formula (p2), $R^{17}$ and $R^{19}$ may each independently represent a linear or branched alkylene group (preferably an alkylene group of 1 to 5 carbon atoms), and the terminal of $R^{19}$ may be bonded with the terminal of $R^{17}$.

In such a case, a cyclic group is formed by $R^{17}$, $R^{19}$, the oxygen atom with which $R^{19}$ is bonded, and the carbon atom with which the oxygen atom and $R^{17}$ are bonded. Such a cyclic group is preferably a 4 to 7-membered ring, and more preferably a 4 to 6-membered ring. Specific examples of the cyclic group include a tetrahydropyranyl group and a tetrahydrofuranyl group.

As the structural unit (a1), it is preferable to use at least one member selected from the group consisting of structural units represented by a general formula (a1-0-1) shown below and structural units represented by a general formula (a1-0-2) shown below.

[Chemical Formula 6]

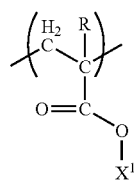
(a1-0-1)

(wherein, R represents a hydrogen atom, a lower alkyl group or a halogenated lower alkyl group; and $X^1$ represents an acid dissociable, dissolution inhibiting group.)

[Chemical Formula 7]

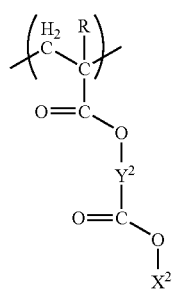
(a1-0-2)

(wherein, R represents a hydrogen atom, a lower alkyl group or a halogenated lower alkyl group; $X^2$ represents an acid dissociable, dissolution inhibiting group; and $Y^2$ represents an alkylene group or an aliphatic cyclic group.)

In the general formula (a1-0-1), the lower alkyl group or halogenated lower alkyl group of R are the same as the lower alkyl group or halogenated lower alkyl group which can be bonded with the a-position of the aforementioned acrylate ester.

$X^1$ is not particularly limited as long as it is an acid dissociable, dissolution inhibiting group. Examples thereof include the aforementioned tertiary alkyl ester-type acid dissociable, dissolution inhibiting groups and acetal-type acid dissociable, dissolution inhibiting groups, and tertiary alkyl ester-type acid dissociable, dissolution inhibiting groups are preferable.

In the general formula (a1-0-2), R is the same as those described above.

$X^2$ is the same as $X^1$ described in the general formula (a1-0-1).

$Y^2$ is preferably an alkylene group of 1 to 4 carbon atoms or a divalent aliphatic cyclic group. As the aliphatic cyclic group, the same as those described above in the explanation of "aliphatic cyclic group" can be used, except that two hydrogen atoms have been removed therefrom.

Specific examples of the structural unit (a1) include structural units represented by the general formulae (a1-1) to (a1-4) shown below.

[Chemical Formula 8]

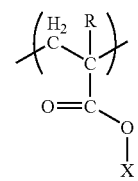
(a1-1)

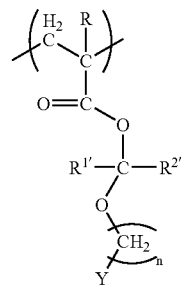
(a1-2)

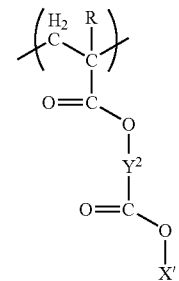
(a1-3)

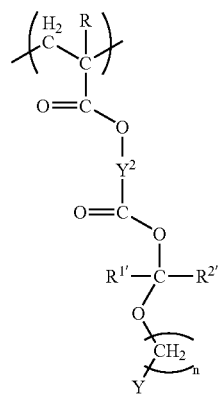
(a1-4)

(wherein $X^1$ represents a tertiary alkyl ester-type acid dissociable, dissolution inhibiting group; Y represents a lower alkyl group of 1 to 5 carbon atoms or an aliphatic cyclic group; n represents an integer of 0 to 3; $Y^2$ represents an alkylene group or an aliphatic cyclic group; R is as defined above; and R1' and R2' each independently represents a hydrogen atom or a lower alkyl group of 1 to 5 carbon atoms.)

It is preferable that at least one of $R^{1'}$ and $R^{2'}$ represent a hydrogen atom, and it is more preferable that both of $R^{1'}$ and $R^{2'}$ represent hydrogen atoms. n is preferably 0 or 1.

Examples of the tertiary alkyl ester-type acid dissociable, dissolution inhibiting group for X' are the same as the above-exemplified tertiary alkyl ester-type acid dissociable, dissolution inhibiting groups for $X^1$.

Examples of the aliphatic cyclic group for Y are the same as those exemplified above in the "aliphatic cyclic group".

$Y^2$ is preferably an alkylene group of 1 to 10 carbon atoms or a divalent aliphatic cyclic group. As the aliphatic cyclic group, the same as those exemplified above in the "aliphatic cyclic group" can be used, except that two hydrogen atoms have been removed therefrom. When $Y^2$ represents an alkylene group of 1 to 10 carbon atoms, it is more preferable that the number of carbon atoms be 1 to 6, still more preferably 1 to 4, and most preferably 1 to 3. When $Y^2$ represents a divalent aliphatic cyclic group, it is particularly preferable that the divalent aliphatic cyclic group be a group in which two or more hydrogen atoms have been removed from a cyclopentane, a cyclohexane, a norbornane, an isobornane, an adamantane, a tricyclodecane or a tetracyclododecane.

Specific examples of structural units represented by general formulae (a1-1) and (a1-4) shown above include the following.

[Chemical Formula 9]

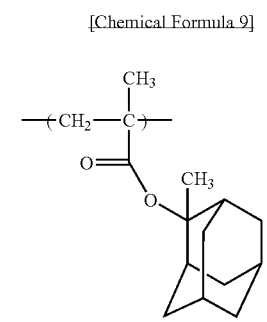
(a1-1-1)

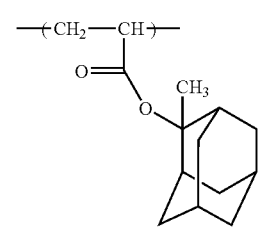
(a1-1-2)

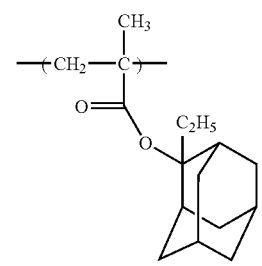
(a1-1-3)

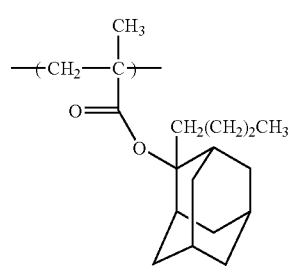
(a1-1-4)

-continued

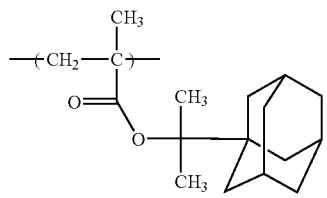
(a1-1-5)

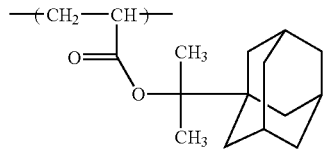
(a1-1-6)

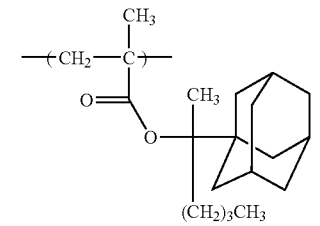
(a1-1-7)

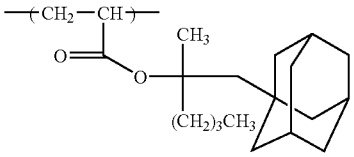
(a1-1-8)

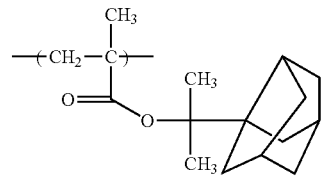
(a1-1-9)

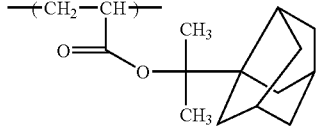
(a1-1-10)

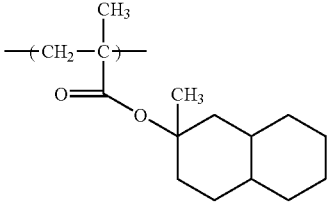
(a1-1-11)

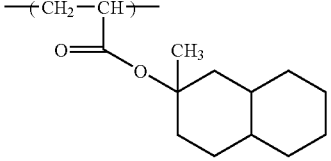
(a1-1-12)

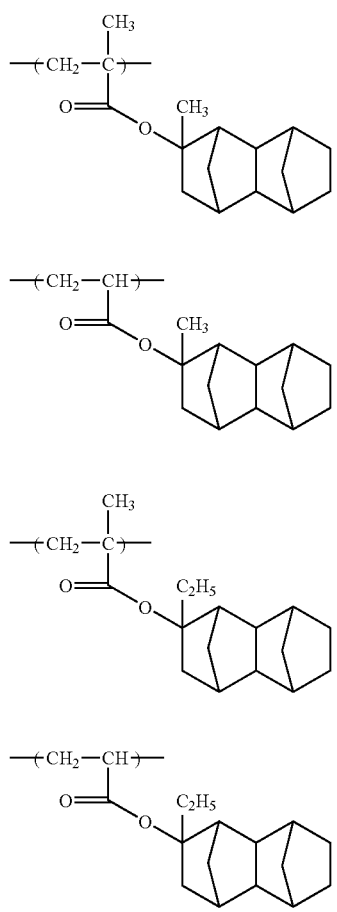
(a1-1-13)
(a1-1-14)
(a1-1-15)
(a1-1-16)
[Chemical Formula 10]
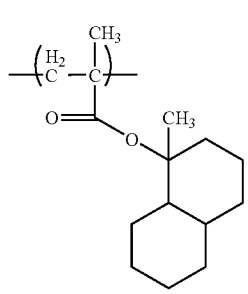
(a1-1-17)
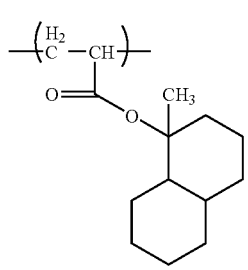
(a1-1-18)
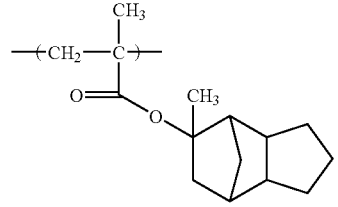
(a1-1-19)
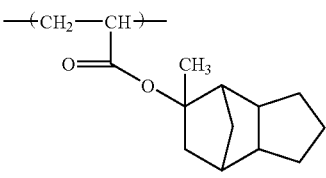
(a1-1-20)
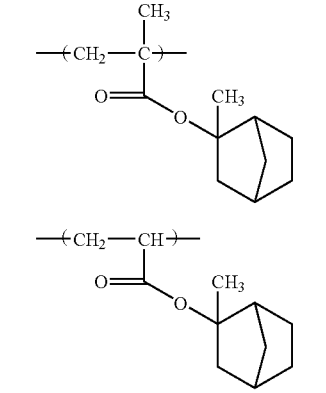
(a1-1-21)
(a1-1-22)
(a1-1-23)
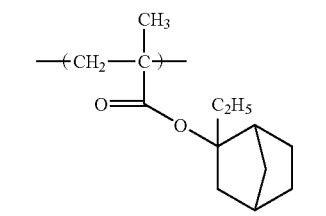
(a1-1-24)
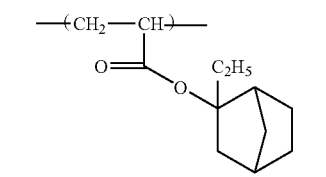
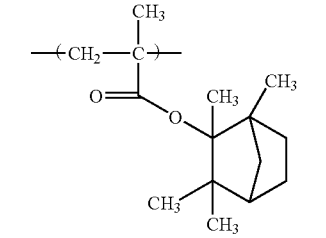
(a1-1-25)
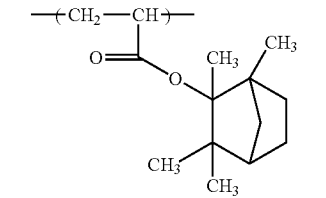
(a1-1-26)

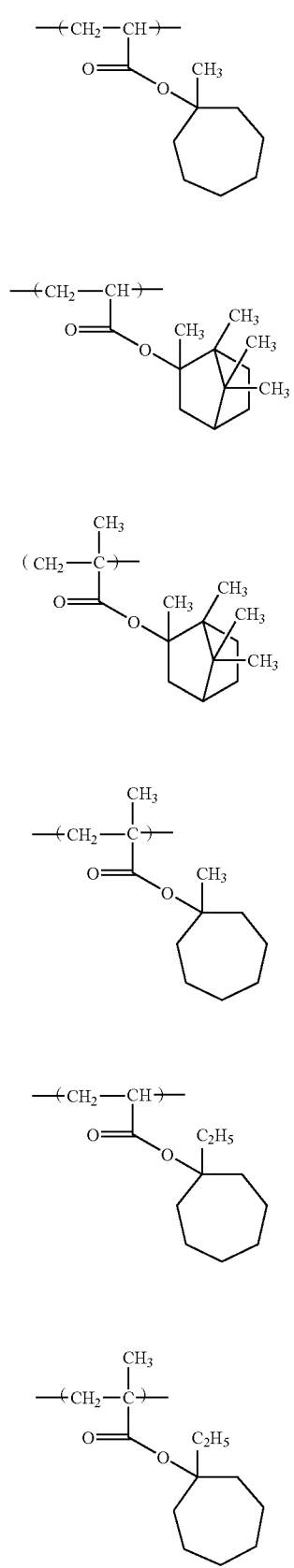
(a1-1-27)
(a1-1-28)
(a1-1-29)
(a1-1-30)
(a1-1-31)
(a1-1-32)
[Chemical Formula 11]
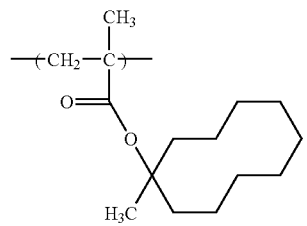
(a1-1-33)
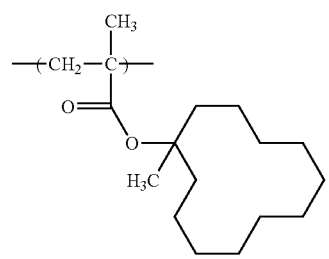
(a1-1-34)
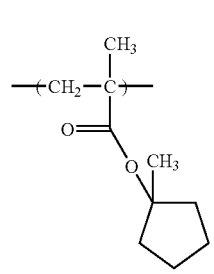
(a1-1-35)
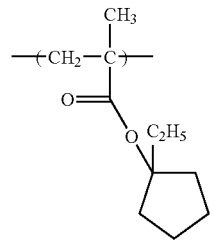
(a1-1-36)
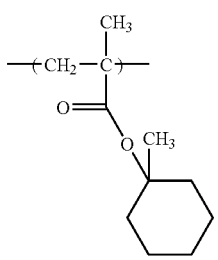
(a1-1-37)
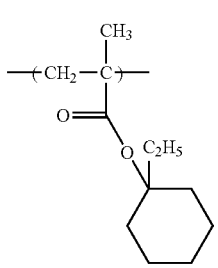
(a1-1-38)

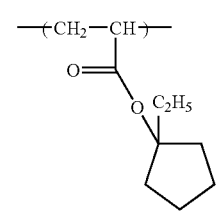 (a1-1-39)
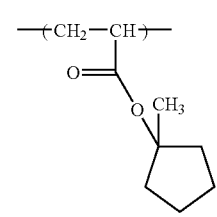 (a1-1-40)
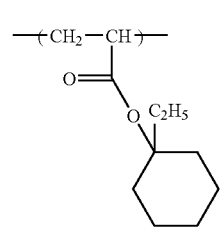 (a1-1-41)
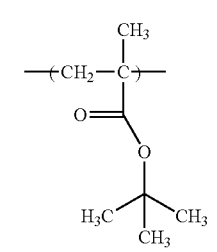 (a1-1-42)
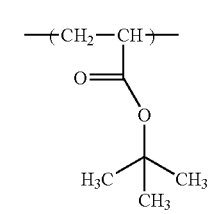 (a1-1-43)
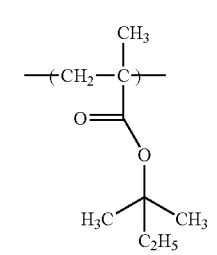 (a1-1-44)
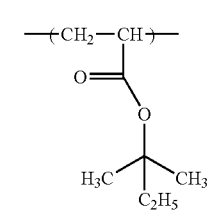 (a1-1-45)
[Chemical Formula 12]
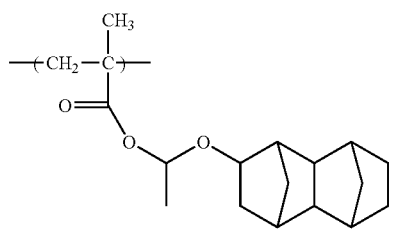 (a1-2-1)
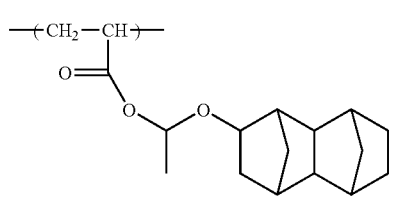 (a1-2-2)
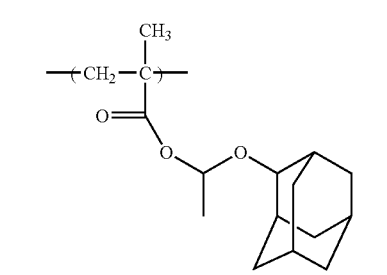 (a1-2-3)
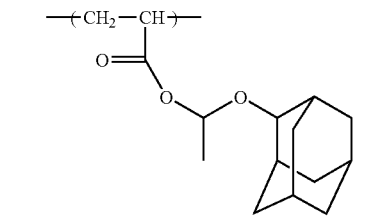 (a1-2-4)
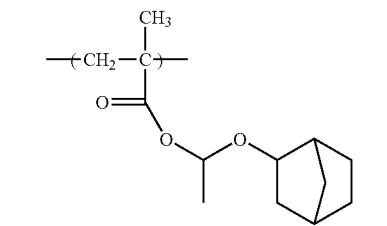 (a1-2-5)
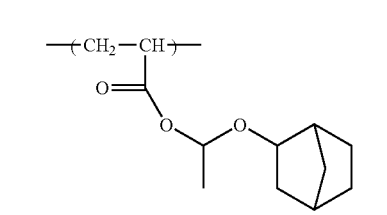 (a1-2-6)

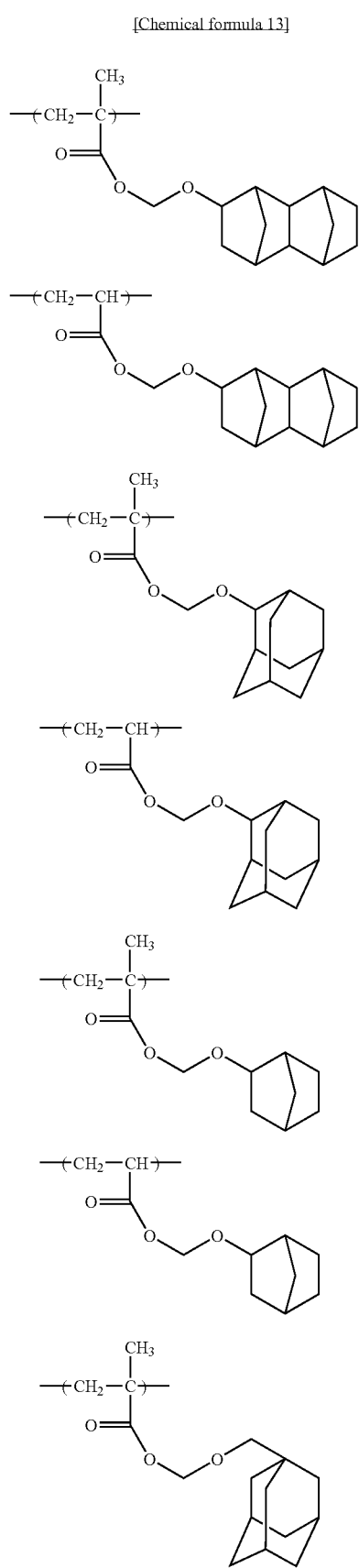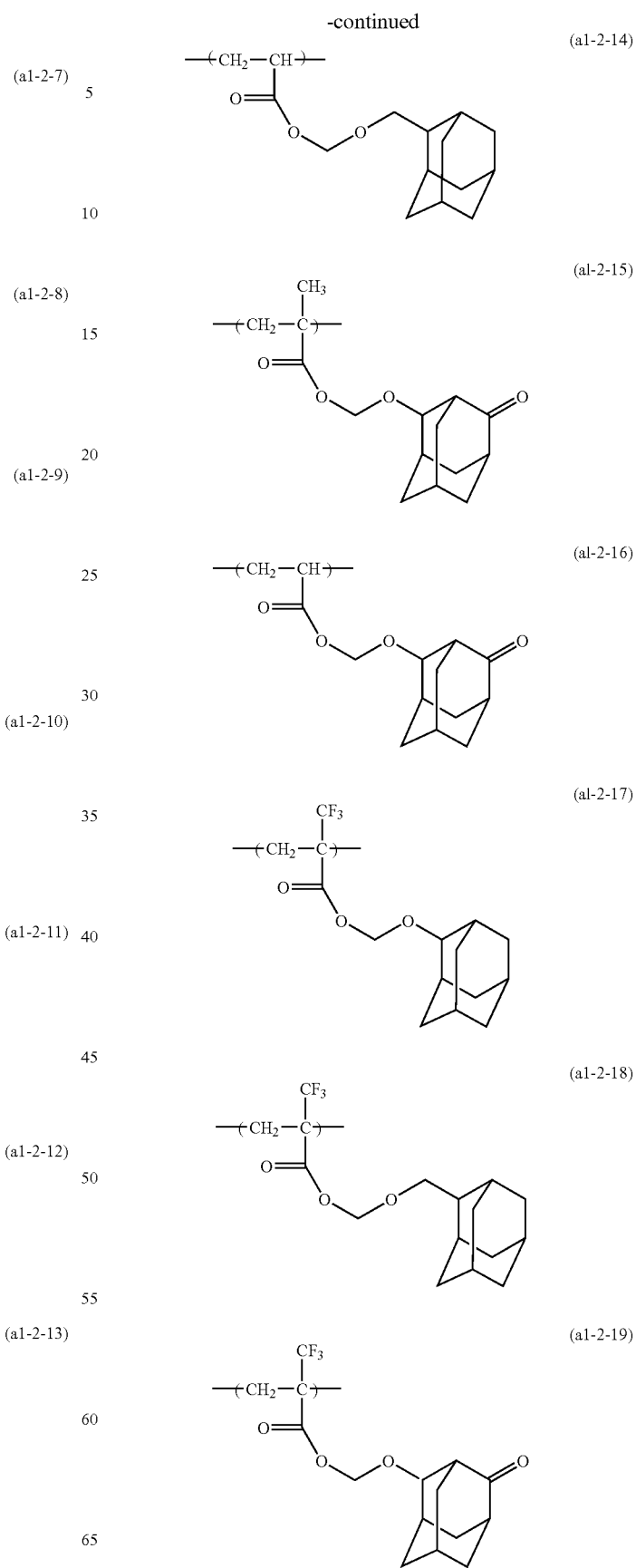

-continued
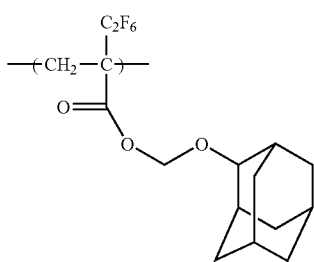
(a1-2-20)
[Chemical Formula 14]
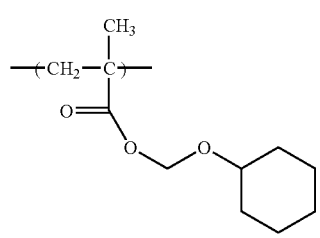
(a1-2-21)
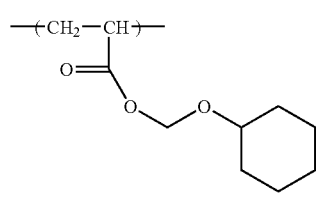
(a1-2-22)
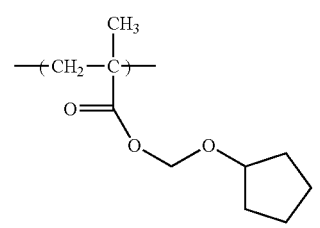
(a1-2-23)
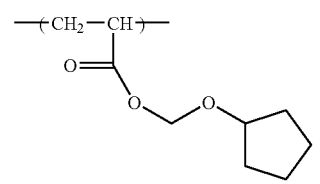
(a1-2-24)
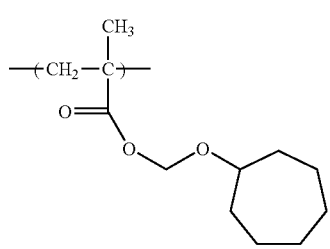
(a1-2-25)
-continued
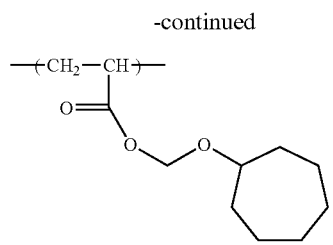
(a1-2-26)
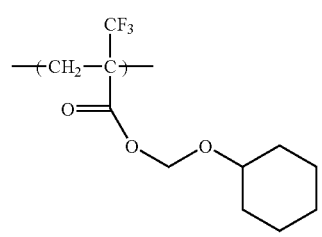
(a1-1-27)
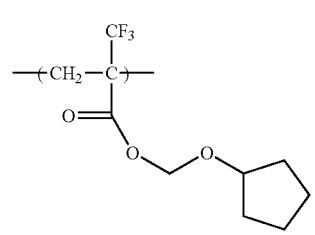
(a1-2-28)
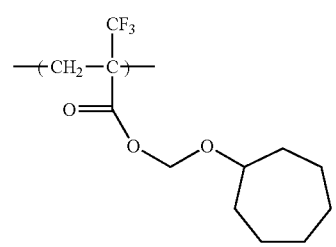
(a1-2-29)
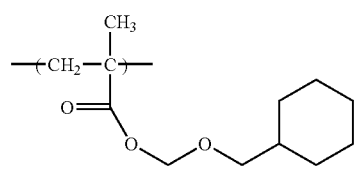
(a1-2-30)
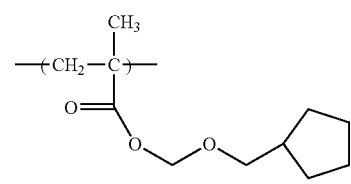
(a1-2-31)
[Chemical Formula 15]
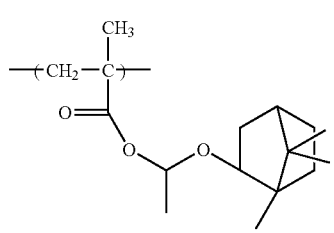
(a1-1-32)

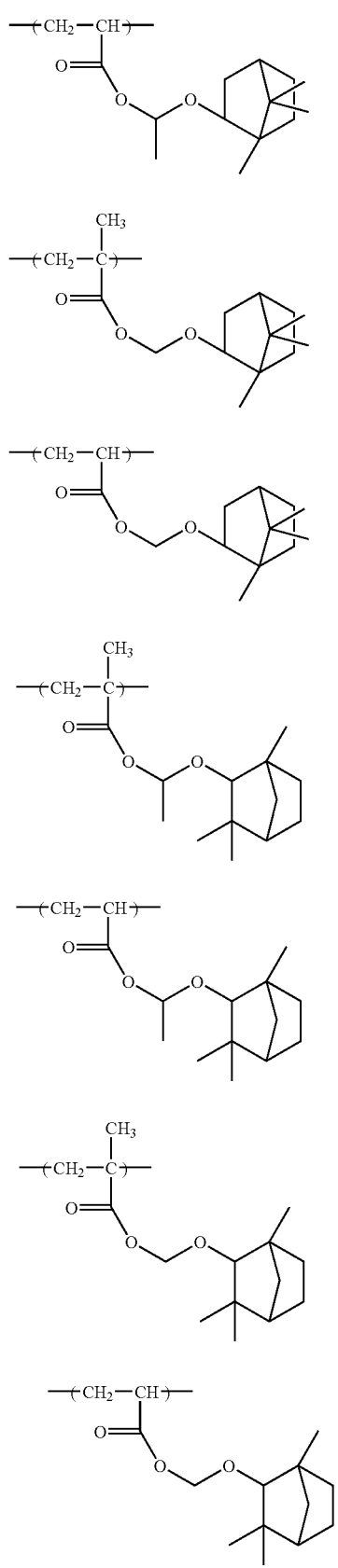
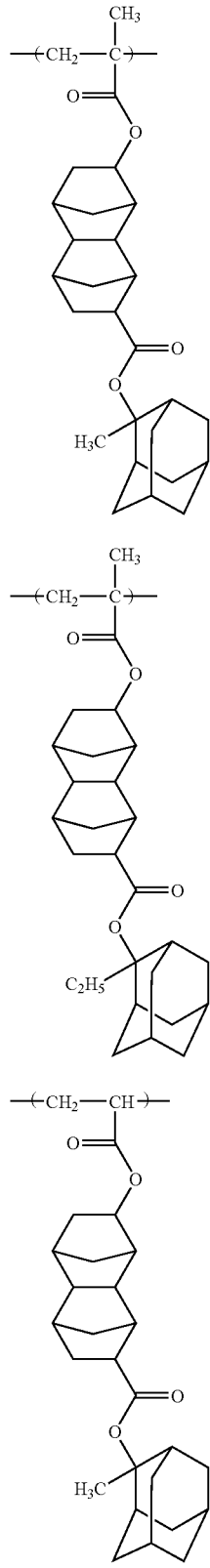
[Chemical Formula 16]

(a1-3-4)
(a1-3-5)
(a1-3-6)
(a1-3-7)
(a1-3-8)
(a1-3-9)

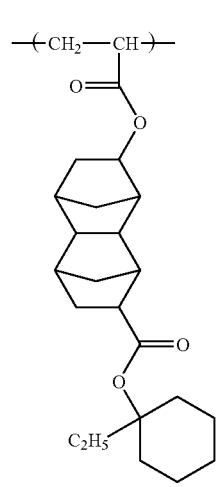
(a1-3-10)
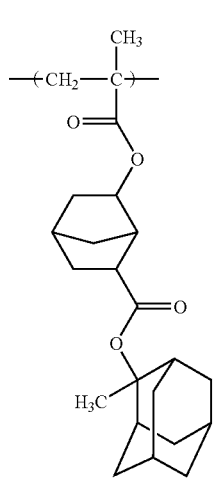
(a1-3-13)
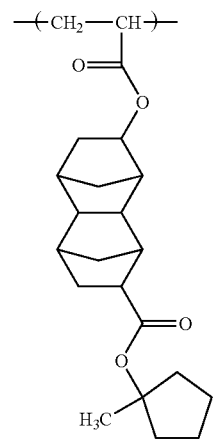
(a1-3-11)
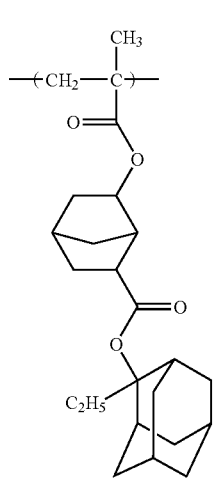
(a1-3-14)
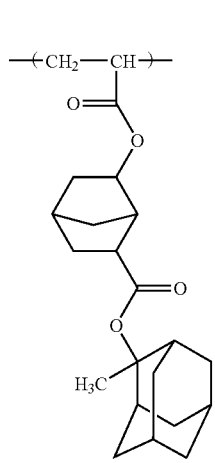
(a1-3-15)
(a1-3-12)

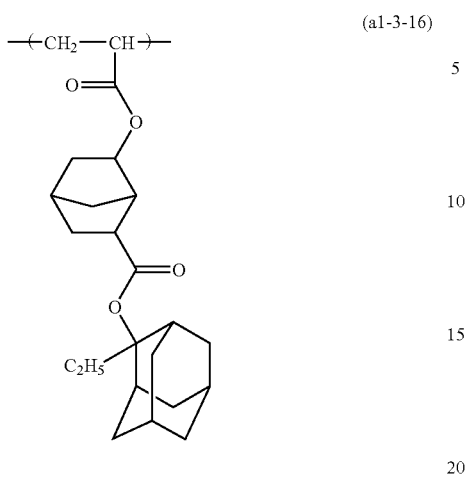
(a1-3-16)
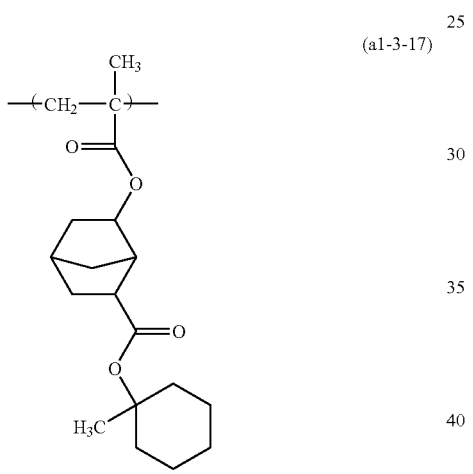
(a1-3-17)
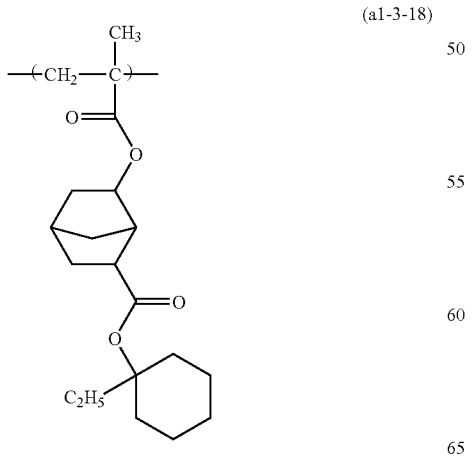
(a1-3-18)
[Chemical Formula 17]
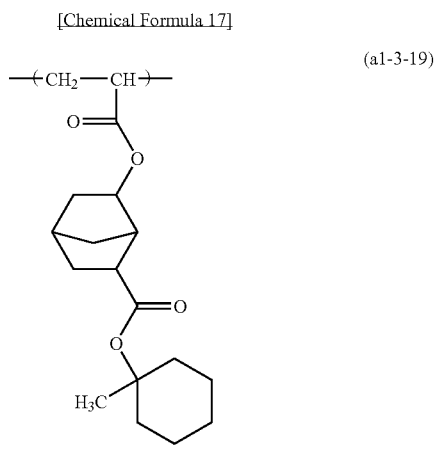
(a1-3-19)
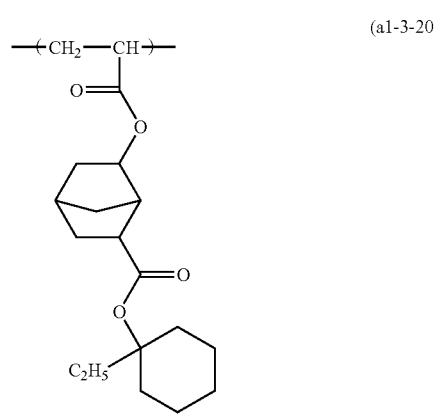
(a1-3-20)
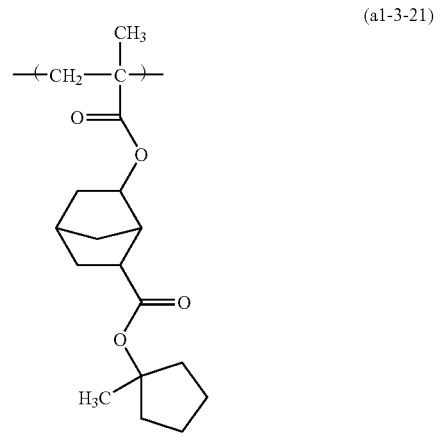
(a1-3-21)

-continued
(a1-3-22)
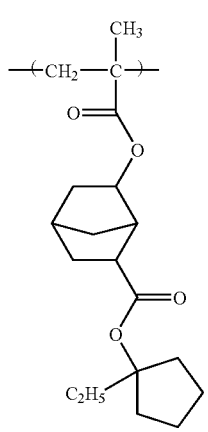
(a1-3-23)
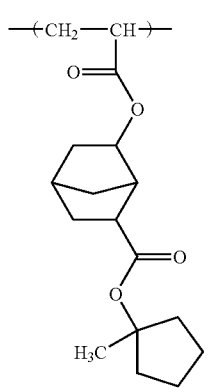
(a1-3-24)
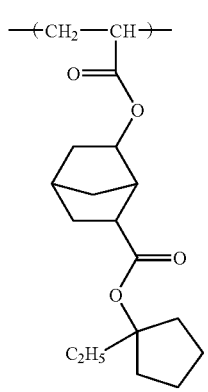
[Chemical Formula 18]
(a1-4-1)
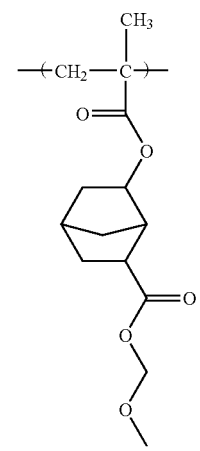
(aq-4-2)
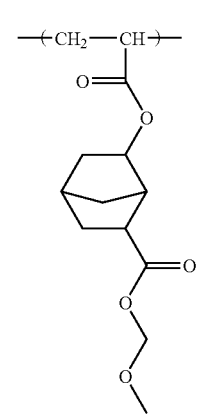
(a1-4-3)
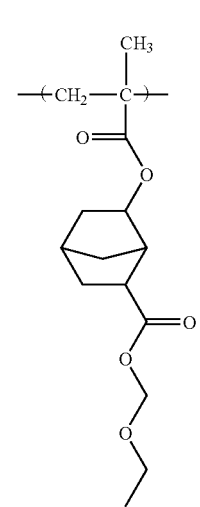

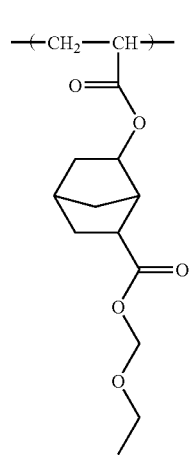 (a1-4-4)
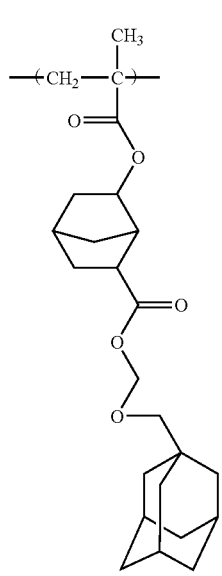 (a1-4-7)
(a1-4-5)
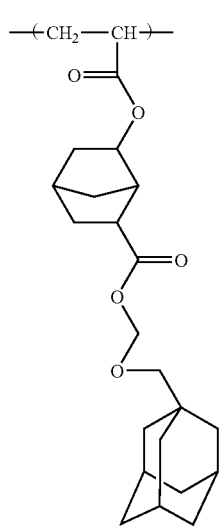 (a1-4-8)
(a1-4-6)
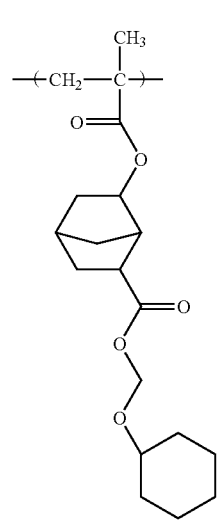 (a1-4-9)

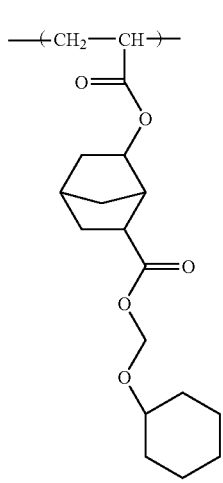 (a1-4-10)
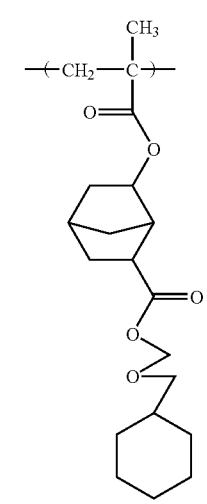 (a1-4-11)
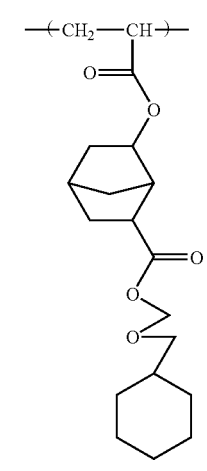 (a1-4-12)
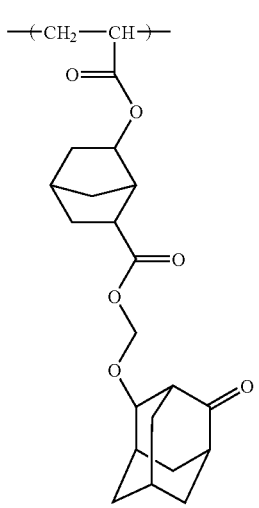 (a1-4-13)
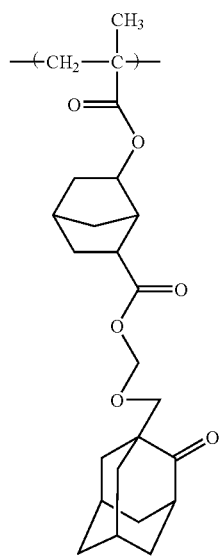 (a1-4-14)
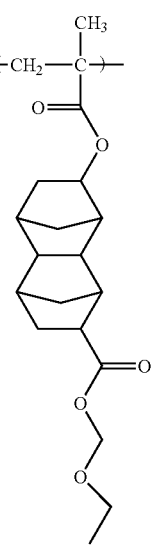 (a1-4-15)

(a1-4-16)
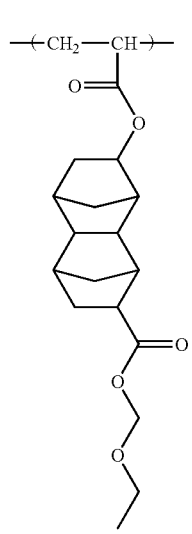
(a1-4-17)
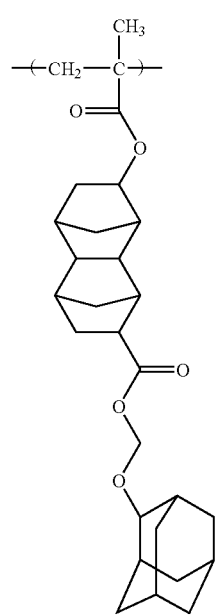
[Chemical Formula 19]
(a1-4-18)
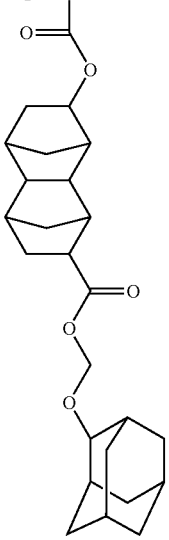
(a1-4-19)
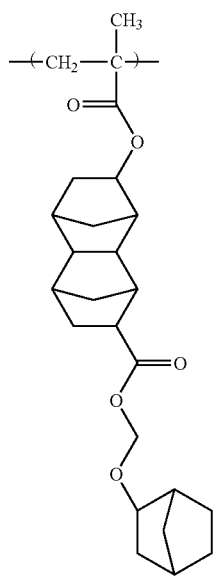

-continued
(a1-4-20)
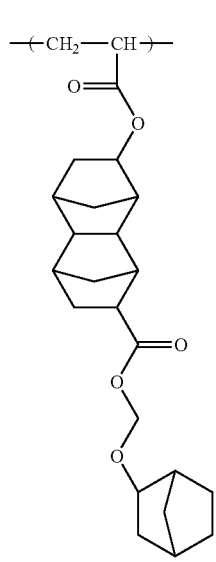
(a1-4-21)
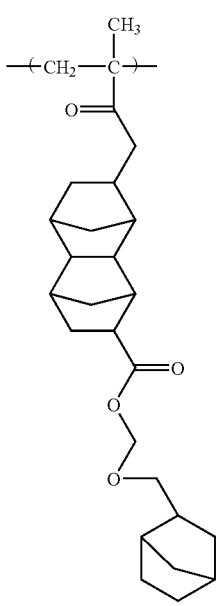
-continued
(a1-4-22)
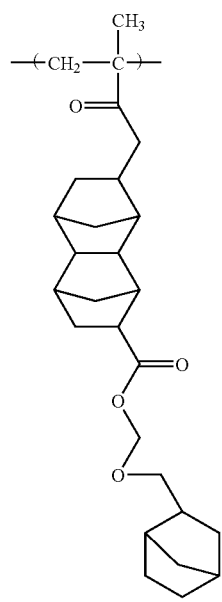
(a1-4-23)
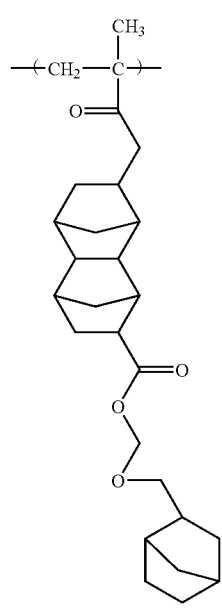

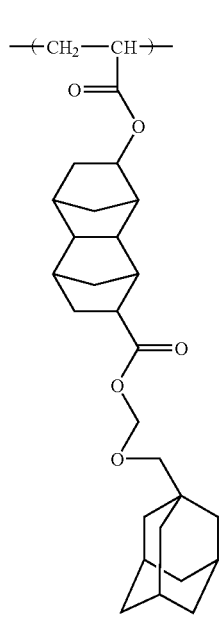 (a1-4-24)
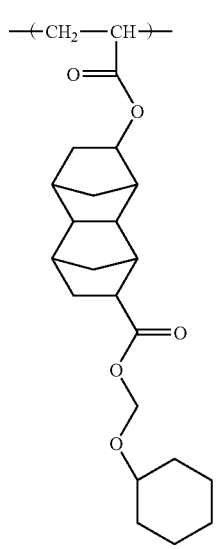 (a1-4-26)
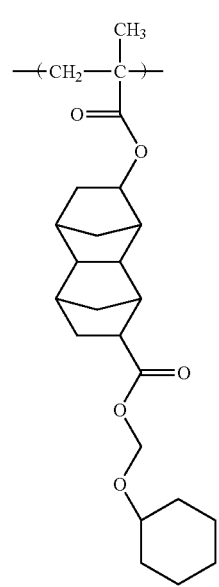 (a1-4-25)
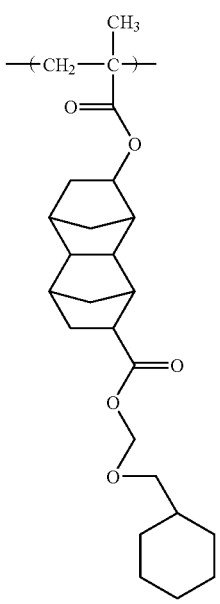 (a1-4-27)

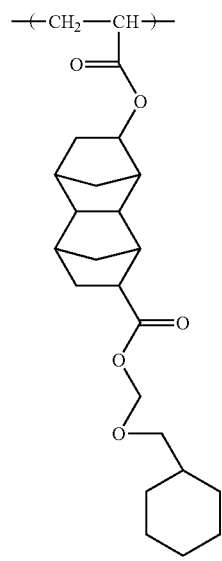
(a1-4-28)
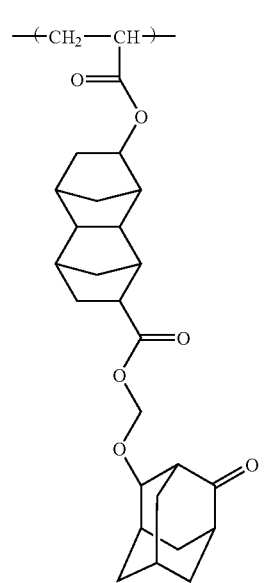
(a1-4-30)
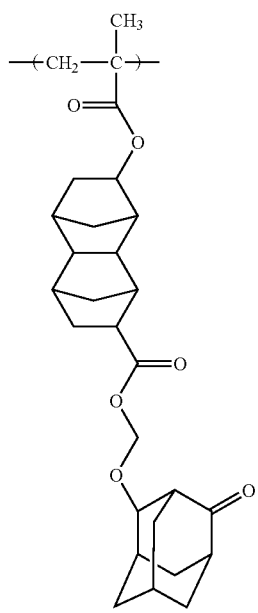
(a1-4-29)
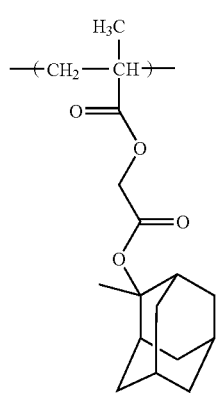
(a1-4-31)
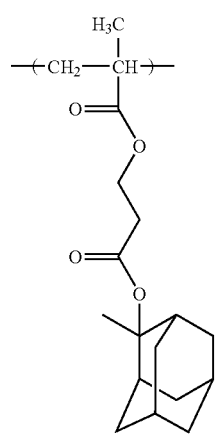
(a1-4-32)

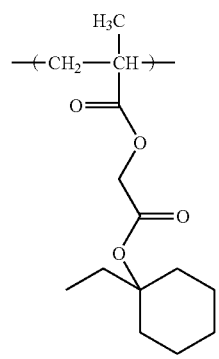
(a1-4-33)
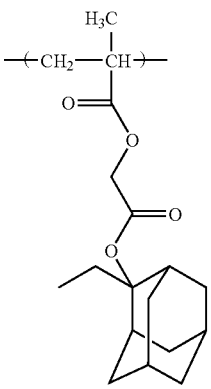
(a1-4-37)
(a1-4-34)
(a1-4-38)
(a1-4-35)
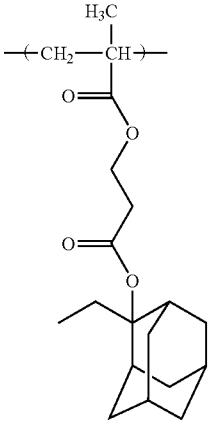
(a1-4-39)
(a1-4-36)
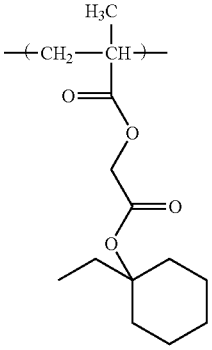
(a1-4-40)
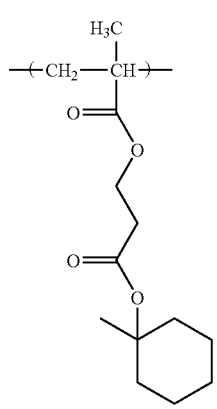

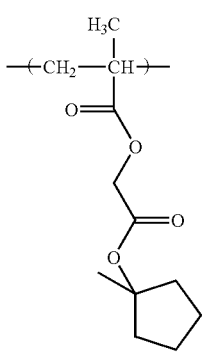

(a1-4-41)

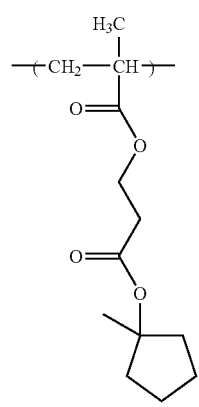

(a1-4-42)

The structural unit (a1) can be used alone, or in combinations of two or more different units.

Among these, structural units represented by the general formula (a1-1) are preferable. More specifically, at least one structural unit selected from the group consisting of structural units represented by the formulae (a1-1-1) to (a1-1-6) and (a1-1-35) to (a1-1-41) is more preferable.

Further, as the structural unit (a1), structural units represented by a general formula (a1-1-01) shown below which includes the structural units represented by formulae (a1-1-1) to (a1-1-4), and structural units represented by a general formula (a1-1-02) shown below which includes the structural units represented by formulae (a1-1-35) to (a1-1-41) are also preferable.

[Chemical Formula 20]

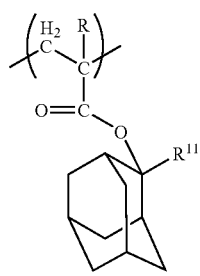

(a1-1-01)

(wherein, R represents a hydrogen atom, a lower alkyl group or a halogenated lower alkyl group; and $R^{11}$ represents a lower alkyl group.)

[Chemical Formula 21]

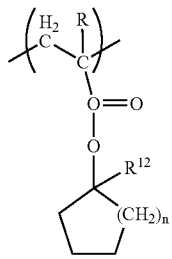

(a1-1-02)

(wherein, R represents a hydrogen atom, a lower alkyl group or a halogenated lower alkyl group; $R^{12}$ represents a lower alkyl group; and h represents an integer of 1 to 3.)

In the general formula (a1-1-01), R is the same as those described above. The lower alkyl group for $R^{11}$ is the same as the lower alkyl group described above in R, and is preferably a methyl group or an ethyl group.

In the general formula (a1-1-02), R is the same as those described above. The lower alkyl group for $R^{12}$ is the same as the lower alkyl group described above in R. $R^{12}$ is preferably a methyl group or an ethyl group, and most preferably an ethyl group. h is preferably 1 or 2, and most preferably 2.

In the component (A1), the amount of the structural unit (a1) based on the combined total of all structural units constituting the component (A1) is preferably 10 to 80 mol %, more preferably 20 to 70 mol %, and still more preferably 25 to 50 mol %. When this proportion is not less than the lower limit in the above range, then a pattern can be easily formed using a positive resist composition which includes the component (A1), whereas when the proportion is not more than the upper limit in the above range, good quantitative balance with the other components can be attained.

Structural Unit (a2)

In the present invention, the component (A1) preferably has a structural unit (a2) derived from an acrylate ester having a lactone-containing cyclic group, in addition to the structural unit (a1).

Here, the term "lactone-containing cyclic group" represents a cyclic group containing a single ring (lactone ring) which has a "—O—C(O)—" structure. This lactone ring is counted as the first ring, and groups that contain only the lactone ring are referred to as monocyclic groups, whereas groups that also contain other ring structures are described as polycyclic groups regardless of the structure of the other rings.

In the case of using the component (A1) to form a resist film, the lactone-containing cyclic group of the structural unit (a2) is effective at improving the adhesion between the resist film and a substrate, and improving compatibility with the developing solution.

The structural unit (a2) can be used arbitrarily without any particular restriction.

Specific examples of the lactone-containing monocyclic group include a group wherein one hydrogen atom is eliminated from ?-butyrolactone. Furthermore, specific examples of the lactone-containing polycyclic group include a group wherein one hydrogen atom is eliminated from a bicycloalkane, a tricycloalkane, or a tetracycloalkane, which contains a lactone ring.

Specific examples of the structural unit (a2) include structural units represented by the general formulae (a2-1) to (a2-5) shown below.

R in the general formulae (a2-1) to (a2-5) represents the same as R described above in the structural unit (a1).

The lower alkyl group for R' is the same as the lower alkyl group for R in the structural unit (a1).

Specific examples of alkylene groups of 1 to 5 carbon atoms for A include a methylene group, ethylene group, n-propylene group and isopropylene group.

In the general formulae (a2-1) to (a2-5), R' is preferably a hydrogen atom in terms of industrial availability.

Specific examples of the structural units represented by the general formulae (a2-1) to (a2-5) include the following.

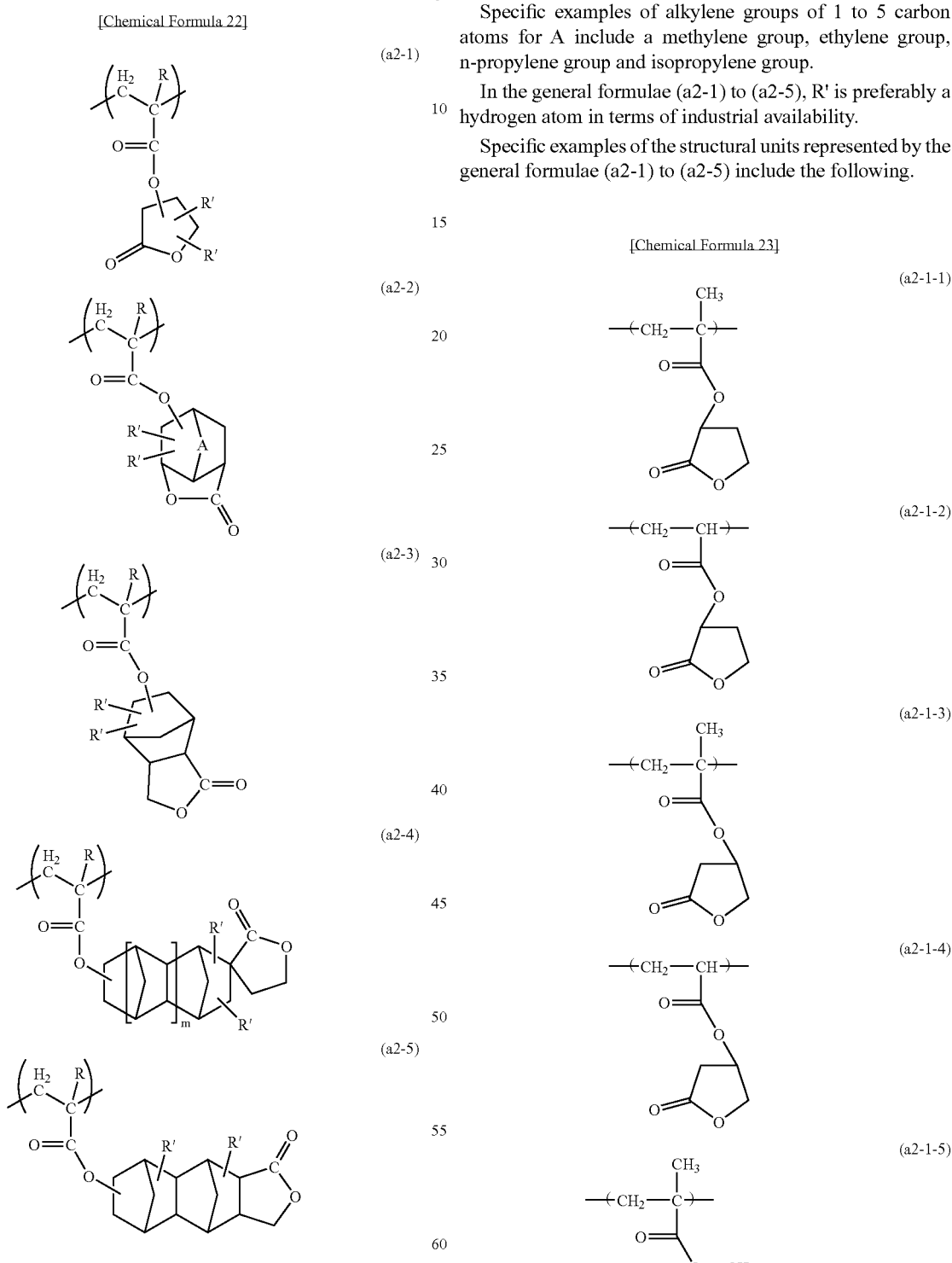

(wherein, R represents a hydrogen atom, a lower alkyl group or a halogenated lower alkyl group; R' represents a hydrogen atom, a lower alkyl group or an alkoxy group of 1 to 5 carbon atoms; m represents an integer of 0 or 11 and A represents an alkylene group of 1 to 5 carbon atoms or an oxygen atom.)

(zs1-1-6)
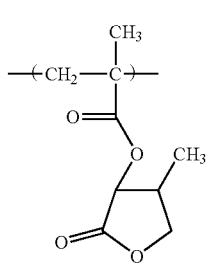
[Chemical Formula 24]
(a2-2-1)
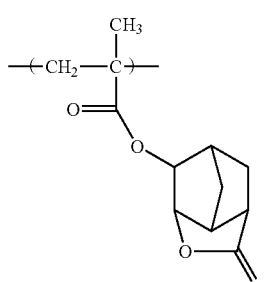
(a2-2-2)
(a2-2-3)
(a2-2-4)
(a2-2-5)
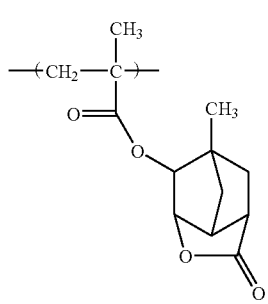
(a2-2-6)
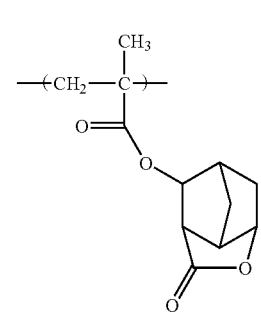
(a2-2-7)
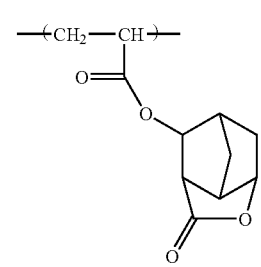
(a2-2-8)
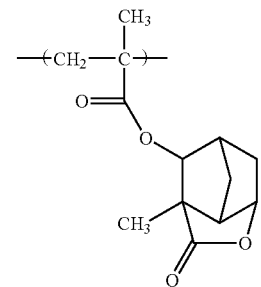
(a2-2-9)
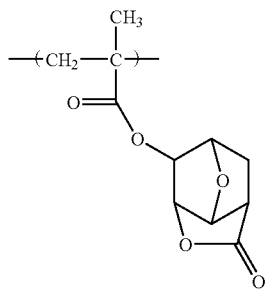

-continued
(a2-2-10)
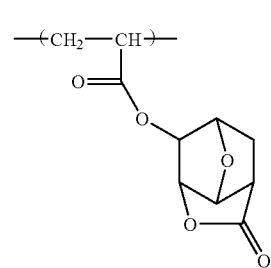
[Chemical Formula 25]
(a2-3-1)
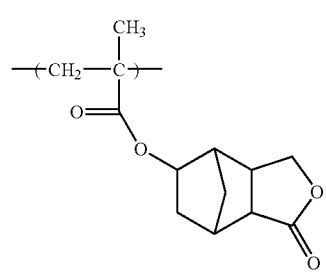
(a2-3-2)
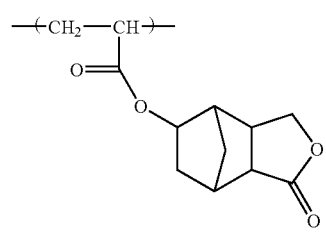
(a2-3-3)
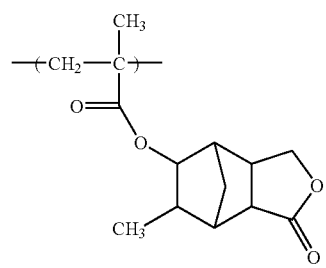
(a2-3-4)
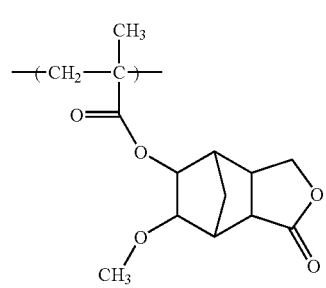
-continued
(a2-3-5)
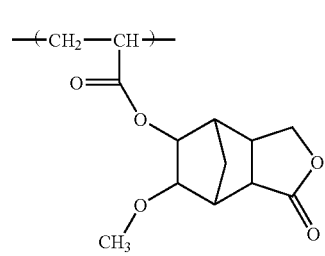
(a2-3-6)
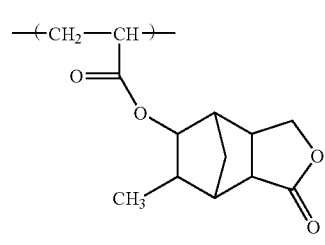
(a2-3-7)
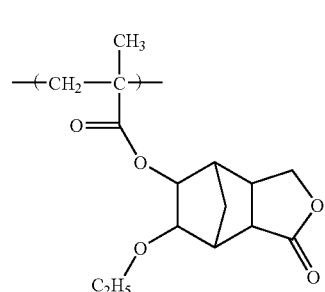
(a2-3-8)
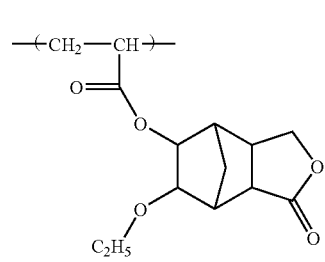
(a2-3-9)
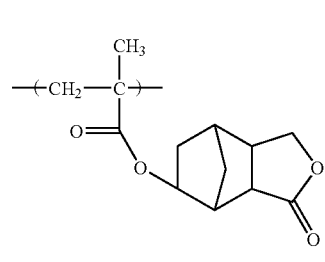
(a2-3-10)
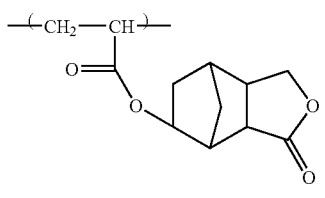

[Chemical Formula 26]
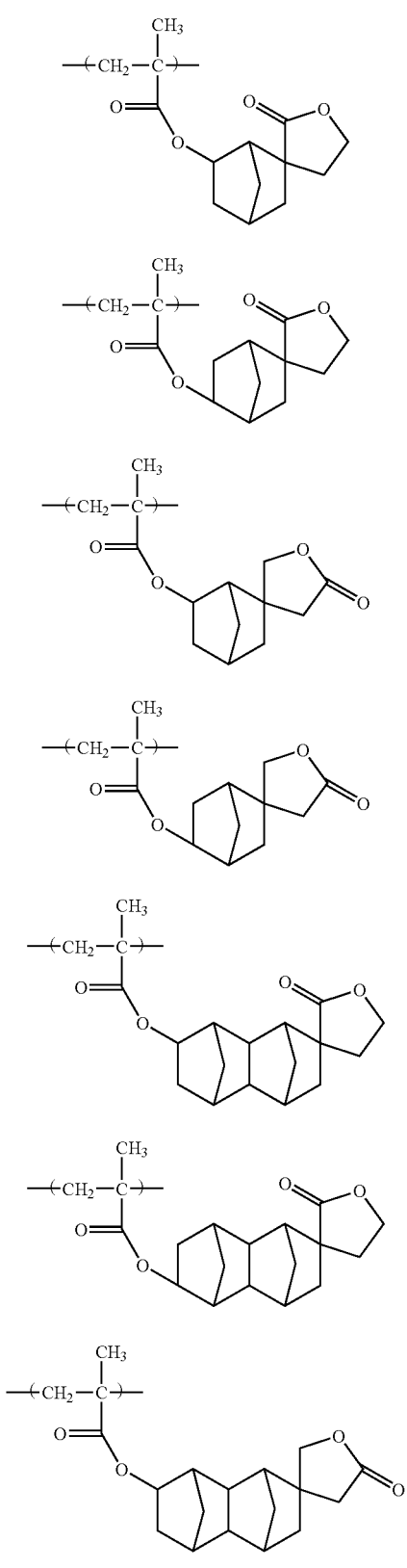
(a2-4-1)
(a2-4-2)
(a2-4-3)
(a2-4-4)
(a2-4-5)
(a2-4-6)
(a2-4-7)
-continued
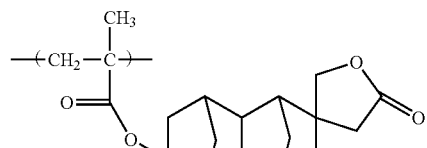 (a2-4-8)
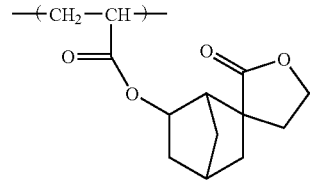 (a2-4-9)
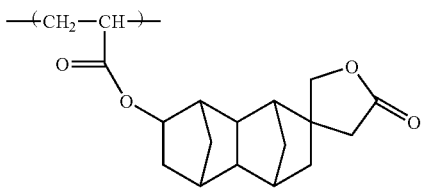 (a2-4-10)
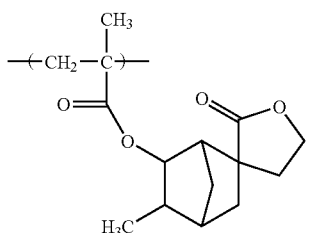 (a2-4-11)
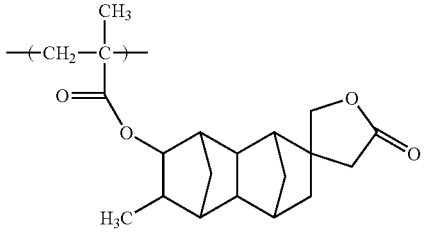 (a2-4-12)
[Chemcial Formula 27]
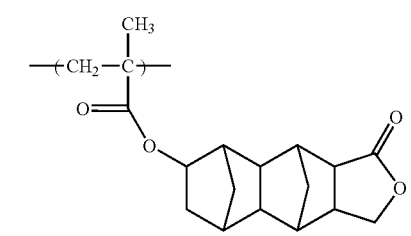 (a2-5-1)
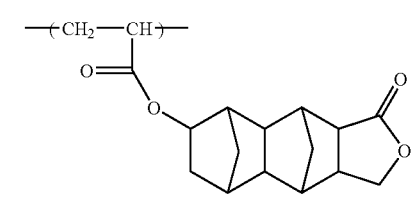 (a2-5-2)

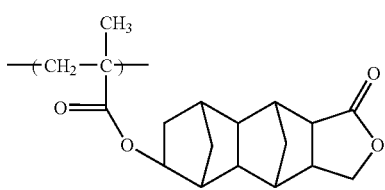
(a2-5-3)

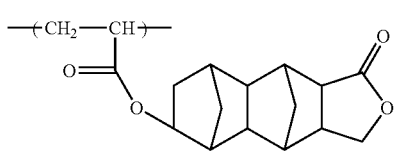
(a2-5-4)

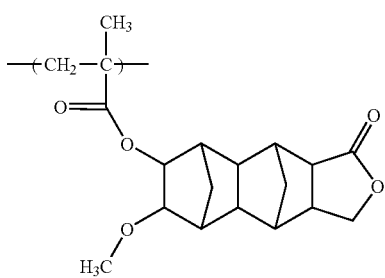
(a2-5-5)

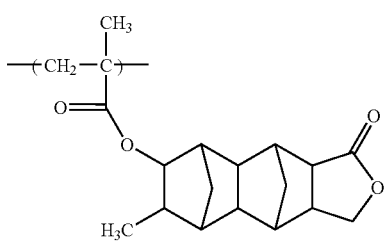
(a2-5-6)

Of these, at least one structural unit selected from the group consisting of formulae (a2-1) to (a2-5) is preferable, and at least one structural unit selected from the group consisting of formulae (a2-1) to (a2-3) is more preferable. Specifically, it is preferable to use at least one structural unit selected from the group consisting of the structural units represented by general formulae (a2-1-1), (a2-1-2), (a2-2-1), (a2-2-2), (a2-3-1), (a2-3-2), (a2-3-9) and (a2-3-10).

In the component (A1), as the structural unit (a2), one structural unit may be used alone, or two or more structural units may be used in combination.

In the component (A1), the amount of the structural unit (a2) based on the combined total of all structural units constituting the component (A1) is preferably 5 to 60 mol %, more preferably 10 to 50 mol %, and still more preferably 20 to 50 mol %. When this proportion is not less than the lower limit in the above range, then the effect by containing the structural unit (a2) can be sufficiently obtained. When the proportion is not more than the upper limit in the above range, good quantitative balance with the other components can be attained.

Structural Unit (a3)

In the present invention, the component (A1) preferably has a structural unit (a3) derived from an acrylate ester having a polar group-containing aliphatic hydrocarbon group, in addition to the structural unit (a1) or the structural units (a1) and (a2).

By including the structural unit (a3), the hydrophilicity of the component (A1) is improved, and hence, the compatibility of the component (A1) with the developing solution is improved. As a result, the solubility of the exposed portions in an alkali developing solution improves, which contributes to favorable improvements in the resolution.

Examples of the polar group include a hydroxyl group, a cyano group, a carboxyl group, a hydroxyalkyl group in which a part of the hydrogen atoms in an alkyl group is substituted with fluorine atoms. Of these, a hydroxyl group is particularly preferable.

Examples of the aliphatic hydrocarbon group include a linear or branched hydrocarbon group of 1 to 10 carbon atoms (preferably an alkylene group), and a polycyclic aliphatic hydrocarbon group (polycyclic group). The polycyclic group can be appropriately selected from the multitude of structural units proposed as resins in resist compositions for ArF excimer lasers and the like. The number of carbon atoms in the polycyclic group is preferably from 7 to 30.

Of these, a structural unit derived from an acrylate ester having the polycyclic aliphatic group which contains a hydroxyl group, a cyano group, a carboxyl group, or a hydroxyalkyl group in which a part of the hydrogen atoms within an alkyl group has been substituted with fluorine atoms (fluorinated alkyl group) is more preferable. Examples of the polycyclic group include groups in which two or more hydrogen atoms have been removed from a bicycloalkane, a tricycloalkane, a tetracycloalkane, or the like. Specific examples include a group in which two or more hydrogen atoms have been removed from a polycycloalkane such as an adamantane, a norbornane, an isobornane, a tricyclodecane, or a tetracyclododecane. Of these polycyclic groups, a group in which two or more hydrogen atoms have been removed from an adamantane, a norbornane, or a tetracyclododecane is industrially preferable.

As the structural unit (a3), for example, a structural unit derived from a hydroxyethyl ester of acrylic acid is preferable, when the hydrocarbon group within the polar group-containing aliphatic hydrocarbon group is a linear or branched hydrocarbon group of 1 to 10 carbon atoms. On the other hand, a structural unit represented by a general formula (a3-1), (a3-2), or (a3-3) is preferable, when the hydrocarbon group is a polycyclic group.

[Chemical Formula 28]

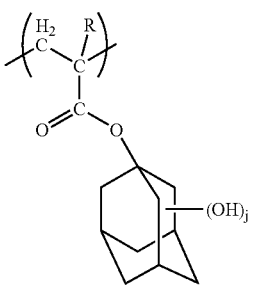
(a3-1)

-continued

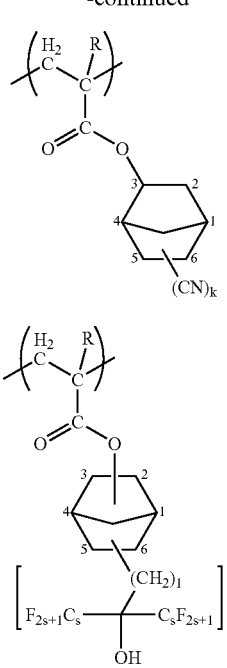

(wherein, R represents the same as defined above; j represents an integer of 1 to 3; k represents an integer of 1 to 3; t' represents an integer of 1 to 3; l represents an integer of 1 to 5; and s represents an integer of 1 to 3.)

In the general formula (a3-1), j is preferably 1 or 2, and more preferably 1. In the case that j is 2, a structural unit in which a hydroxyl group is bonded with the 3-position and 5-position of the adamantyl group is preferable. In the case that j is 1, a structural unit in which a hydroxyl group is bonded with the 3-position of the adamantyl group is preferable.

Of these, it is preferable that j be 1, and the hydroxyl group be bonded with the 3-position of the adamantyl group.

In the general formula (a3-2), k is preferably 1. In the general formula (a3-2), a structural unit in which a cyano group is bonded with the 5-position or 6-position of the norbornyl group is preferable.

In the general formula (a3-3), t' is preferably 1. l is preferably 1. s is preferably 1. Further, in the general formula (a3-3), it is preferable that a 2-norbonyl group or 3-norbonyl group be bonded at the terminal of the carboxy group of the acrylic acid. It is preferable that a fluorinated alkyl alcohol be bonded with the 5-position or 6-position of the norbornyl group.

In the component (A1), as the structural unit (a3), one structural unit may be used alone, or two or more structural units may be used in combination.

In the component (A1), the amount of the structural unit (a3) based on the combined total of all structural units constituting the component (A1) is preferably 5 to 50 mol %, more preferably 5 to 40 mol %, and still more preferably 5 to 25 mol %. When this proportion is not less than the lower limit in the above range, then the effect by containing the structural unit (a3) can be sufficiently obtained, whereas when the proportion is not more than the upper limit in the above range, good quantitative balance with the other components can be attained.

Structural Unit (a4)

The component (A1) may also have a structural unit (a4) which is other than the above-mentioned structural units (a1) to (a3), as long as the effects of the present invention are not impaired.

As the structural unit (a4), any other structural unit which cannot be classified as one of the above structural units (a1) to (a3) can be used without any particular limitations, and any of the multitude of conventional structural units used within resist resins for ArF excimer lasers or KrF excimer lasers (and particularly for ArF excimer lasers) can be used.

The structural unit (a4) is preferably, for example, a structural unit derived from an acrylate ester containing a non-acid-dissociable aliphatic polycyclic group. Examples of the polycyclic group include groups same as those described above in the structural unit (a1), and any of the multitude of conventional polycyclic groups used within the resin component of resist compositions for ArF excimer lasers or KrF excimer lasers (and preferably for ArF excimer lasers) can be used.

In particular, at least one group selected from amongst a tricyclodecanyl group, an adamantyl group, a tetracyclododecanyl group, an isobornyl group, and a norbornyl group is preferable in terms of industrial availability and the like. These polycyclic groups may contain a linear or branched alkyl group of 1 to 5 carbon atoms as a substituent group.

Specific examples of the structural unit (a4) include a structural unit represented by general formulae (a4-1) to (a4-5) shown below.

[Chemical Formula 29]

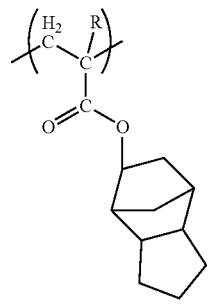

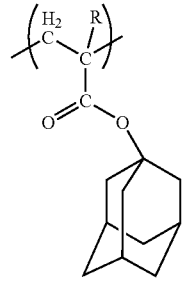

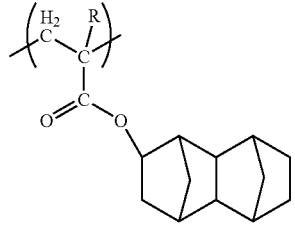

-continued (a4-4)
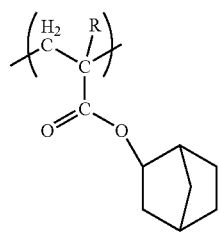

(a4-5)
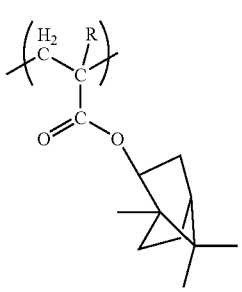

(wherein, R represents the same as those described above.)

When the structural unit (a4) is included in the component (A1), the amount of the structural unit (a4) based on the combined total of all the structural units that constitute the component (A1) is preferably within the range from 1 to 30 mol %, and more preferably from 10 to 20 mol %.

In the present invention, the component (A1) is a resin component (polymer) which exhibits increased solubility in an alkali developing solution under action of acid. As such a resin component (polymer), a copolymer having the structural units (a1), (a2) and (a3) can be preferably used. Examples of such a copolymer include a copolymer consisting of the structural units (a1), (a2) and (a3), and a copolymer consisting of the structural units (a1), (a2), (a3) and (a4).

In the present invention, as the component (A1), one of copolymers (A1-1) to (A1-5) including a combination of structural units represented by general formulae (A1-1) to (A1-5) shown below is preferable.

[Chemical Formula 30]

(A1-1)
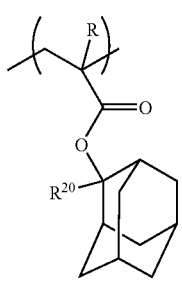 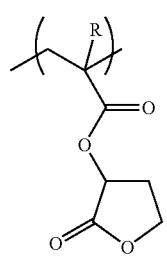 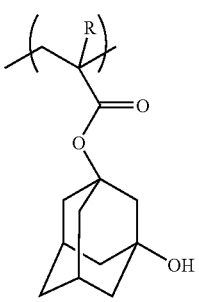

-continued (A1-2)
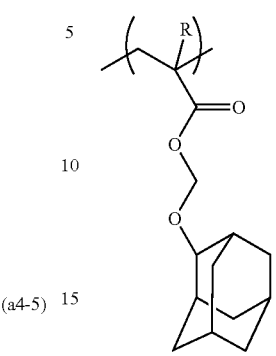 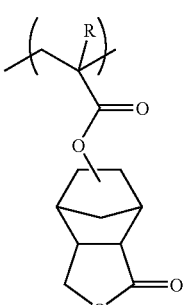 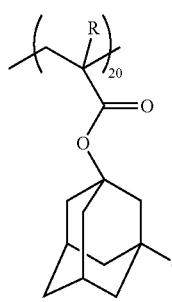

(A1-3)
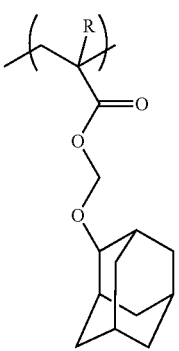 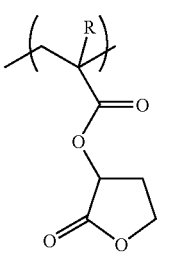 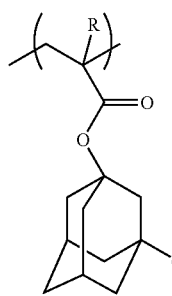

(A1-4)
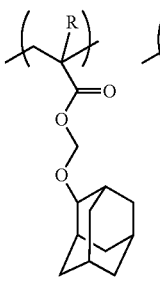 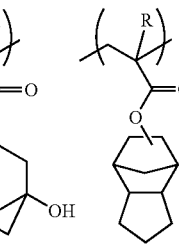

(A1-5)
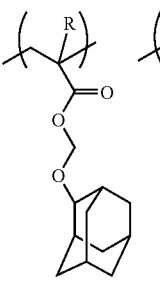 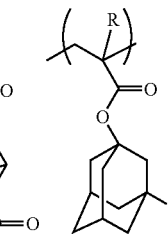

(wherein, R represents the same as those described above; and $R^{20}$ represents a lower alkyl group.)

In the general formulae (A1-1) to (A1-5), R is the same as those described above. Of these, R is preferably a hydrogen atom or a methyl group, and most preferably a methyl group.

In the general formula (A1-1), $R^{20}$ represents a lower alkyl group. Of these, $R^{20}$ is preferably a methyl group or an ethyl group, and most preferably a methyl group.

In the component (A1), each of the copolymers (A1-1) to (A1-5) can be used alone, or in combination of two or more different types.

In the component (A1), in the case of using two or more different types selected from the group consisting of the copolymer (A1-1) to (A1-5) in combination, there is no particular restriction on the number of the copolymers used in combination, and two types of copolymers are preferably used. Examples of the suitable combination of the copolymers include the copolymers (A1-1) and (A1-2), the copolymers (A1-1) and (A1-3), the copolymers (A1-1) and (A1-4), and the copolymers (A1-1) and (A1-5).

There is no particular restriction on the mixture ratio (mass ratio) of the copolymers (A1-1) and (A1-2) (the copolymer (A1-1): the copolymer (A1-2)), and it is preferably within a range from 9:1 to 1:9, more preferably from 8:2 to 2:8, and most preferably 7:3 to 3:7.

The mixing ratio of the copolymers (A1-1) and (A1-3), the copolymers (A1-1) and (A1-4), and the copolymers (A1-1) and (A1-5) is the same as the mixing ratio of the copolymers (A1-1) and (A1-2) described above.

In the component (A1), the total content of the copolymers (A1-1) to (A1-5) is preferably 70% by weight or more, more preferably 80% by weight or more, and may be even 100% by weight.

Of these, the total content of the copolymers (A1-1) to (A1-5) is most preferably 100% by weight.

When the total content is not less than the lower limit of the above range, the lithography properties as a positive resist composition can be improved.

The component (A1) can be obtained, for example, by a conventional radical polymerization or the like of the monomers corresponding with each of the structural units, using a radical polymerization initiator such as azobisisobutyronitrile (AIBN).

Furthermore, in the component (A1), by using a chain transfer agent such as HS—$CH_2$—$CH_2$—$CH_2$—$C(CF_3)_2$—OH, a —$C(CF_3)_2$—OH group can be introduced at the terminals of the component (A1). When a hydroxyalkyl group in which a part of the hydrogen atoms of the alkyl group has been substituted with fluorine atoms is introduced into a copolymer in this manner, the copolymer thus obtained can have an advantageous effect in reducing the levels of developing defects and LER (line edge roughness: non-uniform irregularities within the line side walls).

The weight average molecular weight (Mw) (the polystyrene equivalent value determined by gel permeation chromatography) of the component (A1) is not particularly limited, and is preferably 2,000 to 50,000, more preferably 3,000 to 30,000, still more preferably 4,000 to 20,000, and most preferably 5,000 to 20,000. Ensuring that the weight average molecular weight of the component (A1) is within the range, solubility sufficient for a resist relative to a resist solvent can be obtained, and also excellent dry-etching resistance and excellent sectional shape of the resist pattern can be obtained.

Further, the dispersity (Mw/Mn) is preferably within a range from 1.0 to 5.0, more preferably from 1.0 to 3.0, and most preferably from 1.2 to 2.5. Herein, Mn represents the number average molecular weight.

Further, as the component (A1), an alkali-soluble resin component other than the copolymers (A1-1) to (A1-5), such as other polymeric compounds used in conventional resist compositions, may be used.

In the positive resist composition of the present invention, the content of the component (A1) may be adjusted according to the thickness of the resist film to be formed.

Component (B)

In the resist composition of the present invention, the component (B) includes the acid generator (B1) represented by the general formula (b1-6-1) shown above (hereinafter, referred to as component (B1)), and the acid generator (B2) represented by the general formula (b1-6-2) shown above (hereinafter, referred to as component (B2)).

In the formula, $R^{40}$ is a hydrogen atom or an alkyl group; $R^{41}$ is a halogen atom, a halogenated alkyl group, an alkyl group, an acetyl group, a carboxyl group, or a hydroxyalkyl group; and $R^{42}$ and $R^{43}$ each independently represents a halogen atom, a halogenated alkyl group, an alkyl group, an acetyl group, an alkoxy group, a carboxyl group, or a hydroxylalkyl group.

The alkyl group for $R^{40}$ to $R^{43}$ is preferably a lower alkyl group of 1 to 5 carbon atoms, more preferably a linear or branched alkyl group, still preferably a methyl group, an ethyl group, a propyl group, an isopropyl group, an n-butyl group, a tert-butyl group, a tert-pentyl group, or an isopentyl group, and particularly preferably a methyl group.

The hydroxyalkyl group for $R^{41}$ to $R^{43}$ is preferably an alkyl group in which one or more of hydrogen atoms is/are substituted with hydroxyl group(s). Examples thereof include a hydroxymethyl group, a hydroxyethyl group, and a hydroxypropyl group.

Examples of the halogen atom for $R^{41}$ to $R^{43}$ include a fluorine atom, a chlorine atom, an iodine atom, and a bromine atom. Of these, a fluorine atom is preferable.

The halogenated alkyl group for $R^{41}$ to $R^{43}$ is preferably a halogenated alkyl group of 1 to 5 carbon atoms, more preferably a halogenated alkyl group of 1 to 5 carbon atoms in which hydrogen atoms are substituted with fluorine atoms, and most preferably a trifluoromethyl group and a pentafluoroethyl group.

The alkoxy group for $R^{42}$ and $R^{43}$ is preferably an alkoxy group of 1 to 5 carbon atoms, more preferably a linear or branched alkoxy group, and particularly preferably a methoxy group and an ethoxy group.

$n_0$ to $n_3$ each independently represents an integer of 0 to 3, preferably each independently represents an integer of 0 or 1, and more preferably 0.

However, with respect to $n_0$ and $n_1$, there is a proviso that $n_0+n_1$ is 5 or less.

In the general formula (b1-6-1), each $R^{13}$ is independently a linear or branched alkyl group of 1 to 10 carbon atoms in which at least one hydrogen atom is substituted with fluorine atoms, and preferably a linear alkyl group. The number of carbon atoms in the alkyl group is preferably 1 to 7, and more preferably 1 to 3.

The smaller number of carbon atoms in the alkyl group for $R^{13}$ within the above range enables better solubility in a resist solvent, and is consequently preferable.

The large number of hydrogen atoms substituted with fluorine atoms in the alkyl group for $R^{13}$ increases the strength of acid, and also improves the transparency relative to high-energy light with a wavelength of 200 nm or less or electron beams, and is consequently preferable. The proportion of fluorine atoms in the alkyl group is preferably within a range from 70 to 100%, and more preferably from 90 to 100%. A perfluoroalkyl group wherein all hydrogen atoms are substituted with fluorine atoms is most preferable.

Two of $R^{13}$ may mutually be bonded to form a ring structure. That is, in the general formula (b1-6-1), each $R^{13}$ independently represents a linear or branched alkylene group of 1 to 10 carbon atoms (preferably an alkylene group of 1 to 3 carbon atoms) in which at least one hydrogen atom is/are substituted with fluorine atom(s), and the terminals of two $R^{13}$ may mutually be bonded. The alkylene group is preferably linear.

In such a case, a cyclic group is formed by the constitution composed of two $R^{13}$, two sulfur atoms with which these $R^{13}$ are bonded, and the nitride atom with which these sulfur atoms are bonded. The cyclic group is preferably a 5 to 9-membered ring, more preferably a 6 to 8-membered ring, and most preferably a 6-membered ring.

In the formula (b1-6-2), $R^{14}$ is a linear, branched or cyclic alkyl group, a linear, branched or cyclic halogenated alkyl group, an aryl group, or an alkenyl group, which may contain a substituent group.

The linear or branched alkyl group for $R^{14}$ preferably has 1 to 10 carbon atoms, more preferably 1 to 8 carbon atoms, and most preferably 1 to 4 carbon atoms.

The cyclic alkyl group for $R^{14}$ preferably has 4 to 15 carbon atoms, more preferably 4 to 10 carbon atoms, and most preferably 6 to 10 carbon atoms.

$R^{14}$ is preferably a halogenated alkyl group. That is, in the formula (b1-6-2), $R^{14}SO_3^-$ is preferably a halogenated alkylsulfonate ion. The halogenated alkyl group is a group in which a part of or all of hydrogen atoms of the alkyl group is/are substituted with halogen atoms. Here, the halogenated alkyl group is the same as those described above in "alkyl group" for $R^{40}$ to $R^{43}$ in which a part of or all of hydrogen atoms is/are substituted with halogen atoms. Examples of the halogen atoms which replace the hydrogen atoms include a fluorine atom, a chlorine atom, a bromine atom, and an iodine atom. In the halogenated alkyl group, 50 to 100% of all the hydrogen atoms are preferably substituted with halogen atoms, and it is more preferable that all of the hydrogen atoms are substituted with halogen atoms.

Here, the halogenated alkyl group is preferably a fluorinated alkyl group. The fluorinated alkyl group preferably has 1 to 10 carbon atoms, more preferably has 1 to 8 carbon atoms, and most preferably 1 to 4 carbon atoms. Furthermore, the fluorination rate of the fluorinated alkyl group (proportion of fluorine atoms with which hydrogen atoms are substituted, relative to all hydrogen atoms in the alkyl group before fluorination (hereinafter, referred to as the same)) is preferably within a range from 10 to 100%, more preferably from 50 to 100%, and those wherein all hydrogen atoms are substituted with fluorine atoms are particularly preferable, because the strength of the acid increases.

The aryl group for $R^{14}$ is preferably an aryl group of 6 to 20 carbon atoms.

The alkenyl group for $R^{14}$ is preferably an alkenyl group of 2 to 10 carbon atoms.

Examples of those containing a substituent group in $R^{14}$ include the linear, branched or cyclic alkyl group, the linear, branched or cyclic halogenated alkyl group, or the alkynyl group, in which a part of or all of hydrogen atoms is/are substituted with halogen atoms, hetero atoms, or alkyl groups; and those represented by a general formula (b'-7) shown below. A plurality of substituent groups may be contained.

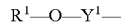    (b'-7)

(wherein, $R^1$ represents a monovalent aliphatic hydrocarbon group, aromatic organic group, or hydroxyalkyl group; and $Y^1$ represents an alkylene group of 1 to 4 carbon atoms in which hydrogen atoms may be substituted with fluorine atoms.)

In the general formula (b'-7), $R^1$ is a monovalent aliphatic hydrocarbon group, aromatic organic group, or hydroxyalkyl group; and $Y^1$ is an alkylene group of 1 to 4 carbon atoms in which hydrogen atoms may be substituted with fluorine atoms.

Examples of the monovalent aliphatic hydrocarbon group include a linear, branched, or cyclic monovalent saturated hydrocarbon group of 1 to 15 carbon atoms, and a linear or branched monovalent aliphatic unsaturated hydrocarbon group of 2 to 5 carbon atoms.

Examples of the linear monovalent saturated hydrocarbon group include a methyl group, an ethyl group, a propyl group, a butyl group, a pentyl group, a hexyl group, a heptyl group, an octyl group, a nonyl group, and a decanyl group.

Examples of the branched monovalent saturated hydrocarbon groups include a 1-methylethyl group, 1-methylpropyl group, 2-methylpropyl group, 1-methylbutyl group, 2-methylbutyl group, 3-methylbutyl group, 1-ethylbutyl group, 2-ethylbutyl group, 1-methylpentyl group, 2-methylpentyl group, 3-methylpentyl group and 4-methylpentyl group.

The cyclic monovalent saturated hydrocarbon group may be either a polycyclic group or a monocyclic group. For example, groups in which one hydrogen atom has been removed from a monocycloalkane or a polycycloalkane such as a bicycloalkane, tricycloalkane or tetracycloalkane can be mentioned. Specific examples include groups in which one hydrogen atom has been removed from a monocycloalkane such as cyclopentane, cyclohexane, cycloheptane or cyclooctane; and groups in which one hydrogen atom has been removed from a polycycloalkane such as adamantane, norbornane, isobornane, tricyclodecane or tetracyclododecane.

Examples of the linear monovalent unsaturated hydrocarbon group include a vinyl group, propenyl group (allyl group) and butynyl group.

Examples of the branched monovalent unsaturated hydrocarbon group include 1-methylpropenyl group and 2-methylpropenyl group.

The monovalent aliphatic hydrocarbon group for $R^1$ preferably has 2 to 4 carbon atoms, and it is particularly preferable that the monovalent aliphatic hydrocarbon group have 3 carbon atoms.

Examples of monovalent aromatic organic groups for $R^1$ include aryl groups in which one hydrogen atom has been removed from an aromatic hydrocarbon ring, such as a phenyl group, a biphenyl group, a fluorenyl group, a naphthyl group, an anthryl group, and a phenanthryl group; heteroaryl groups in which a part of the carbon atoms constituting the ring(s) of these aryl groups is substituted with hetero atoms such as an oxygen atom, a sulfur atom, and a nitrogen atom; and arylalkyl groups such as a benzyl group, a phenethyl group, a 1-naphthylmethyl group, a 2-naphthylmethyl group, 1-naphthylethyl group, and 2-naphthylethyl group. The number of carbon atoms of the alkyl chain in the arylalkyl group is preferably 1 to 4, more preferably 1 or 2, and still more preferably 1. These aryl groups, heteroaryl groups, and arylalkyl groups may contain a substituent group such as an alkyl group of 1 to 10 carbon atoms, a halogenated alkyl group, alkoxy group, a hydroxyl group, and a halogen atom. The number of carbon atoms of the alkyl group or halogenated alkyl group as the substituent group is preferably from 1 to 8, and more preferably from 1 to 4. Also, the halogenated alkyl group is preferably a fluorinated alkyl group. Examples of the halogen atom include a fluorine atom, a chlorine atom, an iodine atom, and a bromine atom. Of these, a fluorine atom is preferable.

The hydroxyalkyl group for $R^1$ is a linear, branched or cyclic, monovalent saturated hydrocarbon group in which at least one hydrogen atom has been substituted with a hydroxyl group. A linear or branched monovalent saturated hydrocarbon group in which one or two hydrogen atoms have been substituted with hydroxyl groups is preferable. Specific examples include a hydroxymethyl group, hydroxyethyl group, 1-hydroxypropyl group, 2-hydroxypropyl group, 3-hydroxypropyl group and 2,3-dihydroxypropyl group.

The monovalent hydroxyalkyl group for $R^1$ preferably has 1 to 10 carbon atoms, more preferably 1 to 8 carbon atoms, still more preferably 1 to 6 carbon atoms, and most preferably 1 to 3 carbon atoms.

Examples of alkylene groups of 1 to 4 carbon atoms for $Y^1$ which may be fluorinated include —$CF_2$—, —$CF_2CF_2$—, —$CF_2CF_2CF_2$—, —$CF(CF_3)CF_2$—, —$CF(CF_2CF_3)$—, —$C(CF_3)_2$—, —$CF_2CF_2CF_2CF_2$—, —$CF(CF_3)CF_2CF_2$—, —$CF_2CF(CF_3)CF_2$—, —$CF(CF_3)CF(CF_3)$—, —$C(CF_3)_2CF_2$—, —$CF(CF_2CF_3)CF_2$—, —$CF(CF_2CF_2CF_3)$—, —$C(CF_3)(CF_2CF_3)$—; —CHF—, —$CH_2CF_2$—, —$CH_2CH_2CF_2$—, —$CH_2CF_2CF_2$—, —$CH(CF_3)CH_2$—, —$CH(CF_2CF_3)$—, —$C(CH_3)(CF_3)$—, —$CH_2CH_2CH_2CF_2$—, —$CH_2CH_2CF_2CF_2$—, —$CH(CF_3)CH_2CH_2$—, —$CH_2CH(CF_3)CH_2$—, —$CH(CF_3)CH(CF_3)$—, —$C(CF_3)_2CH_2$—; —$CH_2$—, —$CH_2CH_2$—, —$CH_2CH_2CH_2$—, —$CH(CH_3)CH_2$—, —$CH(CH_2CH_3)$—, —$C(CH_3)_2$—, —$CH_2CH_2CH_2CH_2$—, —$CH(CH_3)CH_2CH_2$—, —$CH_2CH(CH_3)CH_2$—, —$CH(CH_3)CH(CH_3)$—, —$C(CH_3)_2CH_2$—, —$CH(CH_2CH_3)CH_2$—, —$CH(CH_2CH_2CH_3)$—, and —$C(CH_3)(CH_2CH_3)$—.

As the alkylene group of 1 to 4 carbon atoms for $Y^1$ which may be fluorinated, it is preferable that the carbon atom bonded with S be fluorinated. Examples of such fluorinated alkylene groups include —$CF_2$—, —$CF_2CF_2$—, —$CF_2CF_2CF_2$—, —$CF(CF_3)CF_2$—, —$CF_2CF_2CF_2CF_2$—, —$CF(CF_3)CF_2CF_2$—,—$CF_2CF(CF_3)CF_2$—,—$CF(CF_3)CF$ ($CF_3$)—, —$C(CF_3)_2CF_2$—, —$CF(CF_2CF_3)CF_2$—; —$CH_2CF_2$—, —$CHCH_2CF_2$—, —$CH_2CF_2CF_2$—; —$CH_2CH_2CH_2CF_2$—, —$CH_2CH_2CF_2CF_2$—, and —$CH_2CF_2CF_2CF_2$—.

Among these, —$CF_2CF_2$—, —$CF_2CF_2CF_2$—, and —$CH_2CF_2CF_2$— are preferable, —$CF_2CF_2$— and —$CF_2CF_2CF_2$— are more preferable, and —$CF_2CF_2$— is particularly preferable.

In the present invention, the component (B1) is preferably those wherein two $R^{13}$ are mutually bonded to form a ring structure, and particularly preferably those represented by a general formula (b1-6-10) shown below.

[Chemical Formula 13]

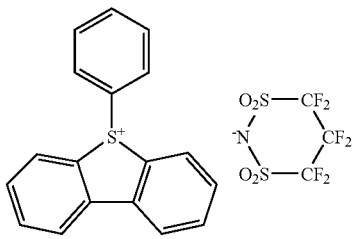

(b1-6-10)

(wherein, $R^{40}$, $R^{41}$, $R^{42}$, $R^{43}$, and $n_0$ to $n_3$ represent the same as those described above; and W'" represents an alkylene group of 2 to 6 carbon atoms in which all hydrogen atoms are substituted with fluorine atoms.)

In the formula, $R^{40}$, $R^{41}$, $R^{42}$, $R^{43}$, and $n_0$ to $n_3$ are the same as those described above.

W'" is an alkylene group of 2 to 6 carbon atoms in which all hydrogen atoms are substituted with fluorine atoms, may be linear or branched, and is preferably linear. The number of carbon atoms in the alkylene group is preferably 2 to 6, more preferably 3 to 5, and most preferably 3. The smaller number of carbon atoms in the alkylene group for W'" within the range enables better solubility in a resist solvent, and is consequently preferable.

Further, a perfluoroalkylene group in which all hydrogen atoms are substituted with fluorine atoms as in the case of W'" enables the strength of acid to be more than an alkylene group containing hydrogen atoms, also improves the transparency relative to high-energy light with a wavelength of 200 nm or less or electron beams, and is consequently preferable.

Particularly preferable examples for the component (B1) include those represented by a general formula (b1-6-11) shown below.

[Chemical Formula 32]

(b1-6-11)

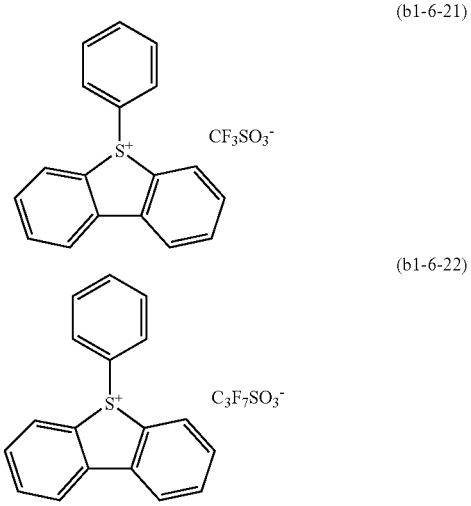

As for the component (B2), it is preferable to contain a linear, branched or cyclic alkyl group as $R^{14}$ in which all hydrogen atoms are substituted with fluorine atoms, and it is more preferable to contain a linear alkyl group as $R^{14}$ in which all hydrogen atoms are substituted with fluorine atoms.

Particularly preferable examples as the component (B2) includes those represented by general formulae (b1-6-21) to (b1-6-23) shown below, and that represented by a general formula (b1-6-23) shown below is most preferable.

[Chemical Formula 33]

(b1-6-21)

(b1-6-22)

-continued

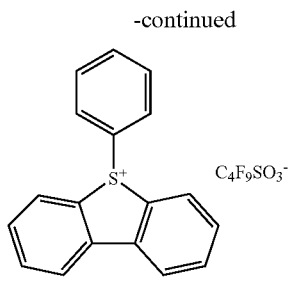
(b1-6-23)

The component (B) includes the components (B1) and (B2), thereby obtaining excellent solubility in commonly-used resist solvents such as propylene glycol monomethyl ether (PGME), propylene glycol monomethyl ether acetate (PGMEA), or ethyl lactate (EL), and also obtaining a resist pattern with excellent verticality and excellent rectangularity, even on an inorganic anti-reflecting film (inorganic BARC) or organic anti-reflecting film (organic BARC), because footing is suppressed on the interface between the resist pattern and the substrate. Further, the component (B) including the components (B1) and (B2) enhances storage stability of the resist, thereby enabling a resist pattern with excellent lithography properties to be formed.

Furthermore, it enables excellent lithography properties to be obtained, when it is used in a resist composition for immersion lithography or a resist composition for forming an upper resist film in a method of forming a resist pattern including a step of an immersion lithography process, or a step of forming a three-layered resist laminate.

Also, the components (B1) and (B2) can be added in large amounts in a resist composition used in a method of forming a resist pattern including a step of conducting immersion lithography or a step of forming a three-layered resist laminate. It is considered that this is attributed to high transparency (effective suppression of photoabsorption) in the exposure wavelength range (especially, wavelength range for ArF excimer laser).

In the component (B), one types of the components (B1) and (B2) each may independently be used alone, or two or more type may be used in combination.

The total content of the components (B1) and (B2) in the component (B) is preferably 70% or more by weight, more preferably 80% or more by weight, and may be 100% by weight. Of these, the total content of the component (B1) and (B2) is most preferably 100% by weight. When the total content is not less than the lower limit, the resist pattern has excellent verticality and excellent rectangularity because footing on the interface between the resist film and the substrate is suppressed, even in the case of using an inorganic or organic anti-reflecting film.

Further, the proportion of the component (B1) based on the combined total of the components (B1) and (B2) in the component (B) is not particularly restricted, and is preferably 10 to 90% by weight, more preferably 20 to 80% by weight, and most preferably 30 to 70% by weight.

When the proportion is within the range, lithography properties can be improved.

Furthermore, in the resist composition of the present invention, the total content of the components (B1) and (B2) is preferably 1 to 30 parts by mass, more preferably 5 to 20 parts by mass, and most preferably 7 to 18 parts by mass, relative to 100 parts by mass of the component (A).

When the total content is not less than the lower limit, the resist pattern has excellent verticality and excellent rectangularity because footing on the interface between the resist pattern and the substrate is suppressed, even in the case of using an inorganic or organic anti-reflecting film. On the other hand, when the total content is not more than the upper limit, storage stability can be excellent.

The component (B) may also have an acid generator (B3) (hereinafter, referred to as component (B3)) which is different to the above-mentioned components (B1) and (B2), as long as the effects of the present invention are not impaired.

As the component (B3), any other acid generators which cannot be classified as one of the above components (B1) and (B2) can be used without any particular limitations, and any of the multitude of conventional acid generators used for chemically-amplified resists can be used.

Examples of these acid generators are numerous, and include onium salt-based acid generators such as iodonium salts and sulfonium salts; oxime sulfonate-based acid generators; diazomethane-based acid generators such as bisalkyl or bisaryl sulfonyl diazomethanes and poly(bis-sulfonyl)diazomethanes; nitrobenzyl sulfonate-based acid generators; iminosulfonate-based acid generators; and disulfone-based acid generators.

As an onium salt-based acid generator, for example, an acid generator represented by a general formula (b-1) or (b-2) shown below can be used.

[Chemical Formula 34]

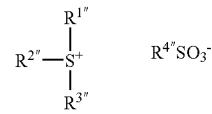
(b-1)

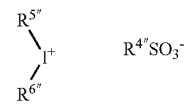
(b-2)

(wherein, $R^{1\prime\prime}$ to $R^{3\prime\prime}$, $R^{5\prime\prime}$ and $R^{6\prime\prime}$ each independently represents an aryl group or an alkyl group; two of $R^{1\prime\prime}$ to $R^{3\prime\prime}$ may mutually be bonded to form a ring together with the sulfur atom; R4″ represents a linear, branched or cyclic alkyl group, or a linear, branched or cyclic fluorinated alkyl group; at least one of $R^{1\prime\prime}$ to $R^{3\prime\prime}$ represents an aryl group; and at least one of $R^{5\prime\prime}$ and $R^{6\prime\prime}$ represents an aryl group.)

In the general formula (b-1), $R^{1\prime\prime}$ to $R^{3\prime\prime}$, each independently represents an aryl group or an alkyl group. Here, two of $R^{1\prime\prime}$ to $R^{3\prime\prime}$ in the formula (b-1) may mutually be bonded to form a ring together with the sulfur atom.

Also, at least one of $R^{1\prime\prime}$ to $R^{3\prime\prime}$ represents an aryl group. Two or more of $R^{1\prime\prime}$ to $R^{3\prime\prime}$ are preferably aryl groups, and all of $R^{1\prime\prime}$ to $R^{3\prime\prime}$ are most preferably aryl groups.

There is no particular restriction on the aryl group of $R^{1\prime\prime}$ to $R^{3\prime\prime}$. For example, the aryl group is an aryl group of 6 to 20 carbon atoms, and a part of or all of hydrogen atoms in the aryl group may be substituted with an alkyl group, an alkoxy group, a halogen atom, a hydroxyl group and the like, or may not be substituted. The aryl group is preferably an aryl group of 6 to 10 carbon atoms because it can be synthesized inexpensively. Specific examples thereof include a phenyl group and a naphthyl group.

In the aryl group, the alkyl group with which hydrogen atoms may be substituted is preferably an alkyl group of 1 to 5 carbon atoms, and most preferably a methyl group, an ethyl group, a propyl group, an n-butyl group, and a tert-butyl group.

In the aryl group, the alkoxy group with which hydrogen atoms may be substituted is preferably an alkoxy group of 1 to 5 carbon atoms, and most preferably a methoxy group, an ethoxy group, n-propoxy group, iso-propoxy group, n-butoxy group, and tert-butoxy group.

In the aryl group, the halogen atom with which hydrogen atoms may be substituted is preferably a fluorine atom.

There is no restriction on the alkyl groups of $R^{1''}$ to $R^{3''}$. Examples thereof include a linear, branched or cyclic alkyl group of 1 to 10 carbon atoms. The number of carbon atoms is preferably 1 to 5, in terms of excellent resolution. Specific examples include a methyl group, an ethyl group, an n-propyl group, an isopropyl group, an n-butyl group, an isobutyl group, an n-pentyl group, a cyclopentyl group, a hexyl group, a cyclohexyl group, a nonyl group, and a decanyl group. Of these, a methyl group is preferable, because it excels in resolution, and can be synthesized inexpensively.

Of these, it is most preferable that $R^{1''}$ to $R^{3''}$ each independently represents a phenyl group or a naphthyl group.

When two of $R^{1''}$ to $R^{3''}$ in the general formula (b-1) may mutually be bonded to form a ring together with the sulfur atom, the ring including the sulfur atom preferably forms a 3 to 10-membered ring, and more preferably forms a 5 to 7-membered ring. Also, when two of $R^{1''}$ to $R^{3''}$ in the general formula (b-1) may mutually be bonded to form a ring together with the sulfur atom, the other of $R^{1''}$ to $R^{3''}$ is preferably an aryl group. The aryl group is the same as those described above in the aryl group for $R^{1''}$ to $R^{3''}$.

$R^{4''}$ represents a linear, branched or cyclic alkyl group, or a linear, branched or cyclic fluorinated alkyl group.

The number of carbon atoms in the linear or branched alkyl group of $R^{4''}$ is preferably from 1 to 10, more preferably from 1 to 8, and most preferably from 1 to 4.

The cyclic alkyl group of $R^{4''}$ represents the same as the cyclic group described above in $R^{1''}$. The number of carbon atoms in the cyclic alkyl group of $R^{4''}$ is preferably from 4 to 15, more preferably from 4 to 10, and most preferably from 6 to 10.

The number of carbon atoms in the fluorinated alkyl group is preferably from 1 to 10, more preferably from 1 to 8, and most preferably from 1 to 4. Furthermore, the fluorination rate of the fluorinated alkyl group (proportion of fluorine atoms in the alkyl group) is preferably within a range from 10 to 100%, more preferably from 50 to 100%, and those wherein all hydrogen atoms are substituted with fluorine atoms are particularly preferable, because the strength of the acid increases.

$R^{4''}$ is most preferably a linear or cyclic alkyl group, or a linear or cyclic fluorinated alkyl group.

In the general formula (b-2), $R^{5''}$ and $R^{6''}$ each independently represents an aryl group or an alkyl group. At least one of $R^{5''}$ and $R^{6''}$ represents an aryl group. Both of $R^{5''}$ and $R^{6''}$ preferably represent aryl groups.

The aryl groups of $R^{5''}$ and $R^{6''}$ represent the same as those described above in "aryl group" of $R^{1''}$ to $R^{3''}$.

The alkyl groups of $R^{5''}$ and $R^{6''}$ represent the sane as those described in "alkyl group" of $R^{1''}$ to $R^{3''}$.

Of these, it is most preferable that both of $R^{5''}$ and $R^{6''}$ be phenyl groups. $R^{4''}$ in the general formula (b-2) represents the same as those described in $R^{4''}$ in the general formula (b-1) shown above.

Specific examples of suitable onium salt-based acid generators represented by formula (b-1) or (b-2) include diphenyliodonium trifluoromethanesulfonate or nonafluorobutanesulfonate; bis(4-tert-butylphenyl)iodonium trifluoromethanesulfonate or nonafluorobutanesulfonate; triphenylsulfonium trifluoromethanesulfonate, heptafluoropropanesulfonate or nonafluorobutanesulfonate; tri(4-methylphenyl)sulfonium trifluoromethanesulfonate, heptafluoropropanesulfonate or nonafluorobutanesulfonate; dimethyl(4-hydroxynaphthyl)sulfonium trifluoromethanesulfonate, heptafluoropropanesulfonate or nonafluorobutanesulfonate; monophenyldimethylsulfonium trifluoromethanesulfonate, heptafluoropropanesulfonate or nonafluorobutanesulfonate; diphenylmonomethylsulfonium trifluoromethanesulfonate, heptafluoropropanesulfonate or nonafluorobutanesulfonate; (4-methylphenyl)diphenylsulfonium trifluoromethanesulfonate, heptafluoropropanesulfonate or nonafluorobutanesulfonate; (4-methoxyphenyl)diphenylsulfonium trifluoromethanesulfonate, heptafluoropropanesulfonate or nonafluorobutanesulfonate; tri(4-tert-butyl)phenylsulfonium trifluoromethanesulfonate, heptafluoropropanesulfonate or nonafluorobutanesulfonate; diphenyl(1-(4-methoxy)naphthyl)sulfonium trifluoromethanesulfonate, heptafluoropropanesulfonate or nonafluorobutanesulfonate; di(1-naphthyl)phenylsulfonium trifluoromethanesulfonate, heptafluoropropanesulfonate or nonafluorobutanesulfonate; 1-phenyltetrahydrothiophenium trifluoromethanesulfonate, heptafluoropropanesulfonate or nonafluorobutanesulfonate; 1-(4-methylphenyl)tetrahydrothiophenium trifluoromethanesulfonate, heptafluoropropanesulfonate or nonafluorobutanesulfonate; 1-(3,5-dimethyl-4-hydroxyphenyl)tetrahydrothiophenium trifluoromethanesulfonate, heptafluoropropanesulfonate or nonafluorobutanesulfonate; 1-(4-methoxynaphthalene-1-yl)tetrahydrothiophenium trifluoromethanesulfonate, heptafluoropropanesulfonate or nonafluorobutanesulfonate; 1-(4-ethoxynaphthalene-1-yl)tetrahydrothiophenium trifluoromethanesulfonate, heptafluoropropanesulfonate or nonafluorobutanesulfonate; 1-(4-n-butoxynaphthalene-1-yl)tetrahydrothiophenium trifluoromethanesulfonate, heptafluoropropanesulfonate or nonafluorobutanesulfonate; 1-phenyltetrahydrothiopyranium trifluoromethanesulfonate, heptafluoropropanesulfonate or nonafluorobutanesulfonate; 1-(4-hydroxyphenyl)tetrahydrothiopyranium trifluoromethanesulfonate, heptafluoropropanesulfonate or nonafluorobutanesulfonate; 1-(3,5-dimethyl-4-hydroxyphenyl)tetrahydrothiopyranium trifluoromethanesulfonate, heptafluoropropanesulfonate or nonafluorobutanesulfonate; and 1-(4-methylphenyl)tetrahydrothiopyranium trifluoromethanesulfonate, heptafluoropropanesulfonate or nonafluorobutanesulfonate.

Also, onium salts in which anionic sites of these onium salts are substituted with a methanesulfonate, an n-propanesulfonate, an n-butanesulfonate, or an n-octanesulfonate can be used.

Further, an onium salt-based acid generator in which the anionic site in the general formula (b-1) or (b-2) is substituted with an anionic site represented by a general formula (b-3) or (b-4) shown below can also be used. Here, the cationic site is the same as those described in the general formula (b-1) or (b-2).

[Chemical Formula 35]

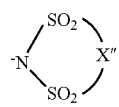

(b-3)

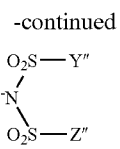
(b-4)

(wherein, X″ represents an alkylene group of 2 to 6 carbon atoms in which at least one hydrogen atom is substituted with a fluorine atom; and Y″ and Z″ each independently represents an alkyl group of 1 to 10 carbon atoms in which at least one hydrogen atom is substituted with a fluorine atom.)

X″ represents a linear or branched alkylene group in which at least one hydrogen atom is substituted with a fluorine atom. The number of carbon atoms in the alkylene group of X″ is from 2 to 6, preferably from 3 to 5, and most preferably 3.

Y″ and Z″ each independently represents a linear or branched alkyl group in which at least one hydrogen atom is substituted with a fluorine atom. The number of carbon atoms in the alkyl group of Y″ and Z″ is from 1 to 10, preferably from 1 to 7, and more preferably from 1 to 3.

Lower numbers of carbon atoms within the alkylene group X″ or the alkyl groups Y″ and Z″ result in better solubility within the resist solvent, and are consequently preferred.

Furthermore, in the alkylene group X″ or the alkyl groups Y″ and Z″, a higher number of hydrogen atoms that have been substituted with fluorine atoms results in increasing the strength of an acid and also improving the transparency relative to high energy light beams of 200 nm or less, or electron beams, and is consequently preferred. The proportion of fluorine atoms in the alkylene group or alkyl group, that is, the fluorination rate, is preferably within a range from 70 to 100%, more preferably from 90 to 100%. A perfluoroalkylene group or a perfluoroalkyl group wherein all hydrogen atoms are substituted with fluorine atoms is most preferable.

In the present specification, the term "oxime sulfonate-based acid generator" represents a compound which has at least one of the groups represented by a general formula (B-1) shown below, and has a property that generates an acid upon exposure to radiation. These kinds of oxime sulfonate-based acid generators are widely used for a chemically-amplified resist composition, so any oxime sulfonate-based acid generator can be used arbitrarily selected from these.

[Chemical Formula 36]

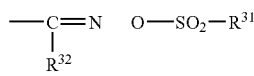
(B-1)

(In the formula (B-1), $R^{31}$ and $R^{32}$ each independently represents an organic group.)

The organic group for $R^{31}$ or $R^{32}$ is a group containing carbon atoms, and may further contain atoms other than carbon atoms (for example, a hydrogen atom, an oxygen atom, a nitrogen atom, a sulfur atom and a halogen atom (a fluorine atom, a chlorine atom and the like)).

The organic group of $R^{31}$ is preferably a linear, branched or cyclic alkyl group or an aryl group. The alkyl group or aryl group may contain a substituent group. There is no particular restriction on the substituent group, and examples thereof include a fluorine atom, and a linear, branched or cyclic alkyl group of 1 to 6 carbon atoms. Here, the term "containing a substituent group" represents that a part of or all of hydrogen atoms in the alkyl group or aryl group is/are substituted with substituent groups.

The number of carbon atoms in the alkyl group of $R^{31}$ is preferably from 1 to 20, more preferably from 1 to 10, still more preferably from 1 to 8, still more preferably from 1 to 6, and most preferably from 1 to 4. The alkyl group for $R^{31}$ is particularly preferably an alkyl group which is partially or completely halogenated (hereinafter, sometimes referred to as a halogenated alkyl group). Here, a partially halogenated alkyl group represents an alkyl group in which a part of the hydrogen atoms is substituted with halogen atoms, and a completely halogenated alkyl group represents an alkyl group in which all of the hydrogen atoms are substituted with halogen atoms. Examples of the halogen atoms include a fluorine atom, a chlorine atom, a bromine atom and an iodine atom. Of these, a fluorine atom is preferable. That is, a halogenated alkyl group is preferably a fluorinated alkyl group.

The number of carbon atoms in the aryl group of $R^{31}$ is preferably from 4 to 20, more preferably from 4 to 10, and most preferably from 6 to 10. The aryl group is particularly preferably an aryl group which is partially or completely halogenated. Here, a partially halogenated aryl group represents an aryl group in which a part of the hydrogen atoms is substituted with halogen atoms, and a completely halogenated aryl group represents an aryl group in which all of the hydrogen atoms are substituted with halogen atoms.

$R^{31}$ is particularly preferably an alkyl group of 1 to 4 carbon atoms containing no substituent group, or a fluorinated alkyl group of 1 to 4 carbon atoms.

The organic group of $R^{32}$ is preferably a linear, branched or cyclic alkyl group, an aryl group, or a cyano group. The alkyl group or aryl group of $R^{32}$ represents the same as those described above in the alkyl group or aryl group of $R^{31}$.

$R^{32}$ is particularly preferably a cyano group, an alkyl group of 1 to 8 carbon atoms containing no substituent group, or a fluorinated alkyl group of 1 to 8 carbon atoms.

The oxime sulfonate-based acid generator is more preferably a compound represented by a general formula (B-2) or (B-3) shown below.

[Chemical Formula 37]

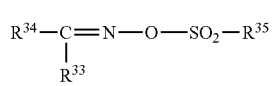
(B-2)

(in the general formula (B-2), $R^{33}$ represents a cyano group, an alkyl group containing no substituent group, or a halogenated alkyl group; $R^{34}$ represents an aryl group; and $R^{35}$ represents an alkyl group containing no substituent group, or a halogenated alkyl group.)

[Chemical Formula 38]

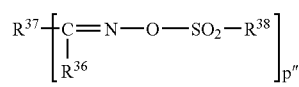
(B-3)

(in the general formula (B-3), $R^{36}$ represents a cyano group, an alkyl group containing no substituent group, or a halogenated alkyl group; $R^{37}$ represents a bivalent or trivalent aromatic hydrocarbon atom; $R^{38}$ represents an alkyl group containing no substituent group or a halogenated alkyl group; and p" represents an integer of 2 or 3.)

In the general formula (B-2), the number of carbon atoms in the alkyl group containing no substituent group or the halogenated alkyl group for $R^{33}$ is preferably from 1 to 10, more preferably from 1 to 8, and most preferably from 1 to 6. $R^{33}$ is preferably a halogenated alkyl group, and more preferably a fluorinated alkyl group.

The fluorinated alkyl group of $R^{33}$ is preferably a group in which 50% or more of the hydrogen atoms in the alkyl group are fluorinated, more preferably a group in which 70% or more of the hydrogen atoms in the alkyl group are fluorinated, and still more preferably a group in which 90% or more of the hydrogen atoms in the alkyl group are fluorinated.

Examples of the aryl group represented by $R^{34}$ include groups in which one hydrogen atom has been removed from an aromatic hydrocarbon ring, such as a phenyl group, a biphenyl group, a fluorenyl group, a naphthyl group, an anthryl group, and a phenantryl group; and heteroaryl groups in which a part of the carbon atoms which constitutes the ring(s) of these groups are substituted with heteroatoms such as an oxygen atom, a sulfur atom, and a nitrogen atom. Of these, a fluorenyl group is preferable.

The aryl group of $R^{34}$ may contain a substituent group such as an alkyl group, a halogenated alkyl group and an alkoxy group of 1 to 10 carbon atoms. The number of carbon atoms of the alkyl group or halogenated alkyl group in the substituent group is preferably from 1 to 8, and more preferably from 1 to 4. Also, the halogenated alkyl group is preferably a fluorinated alkyl group.

The number of carbon atoms in the alkyl group containing no substituent group or the halogenated alkyl group for $R^{35}$ is preferably from 1 to 10, more preferably from 1 to 8, and most preferably from 1 to 6.

$R^{35}$ is preferably a halogenated alkyl group, and more preferably a fluorinated alkyl group.

The fluorinated alkyl group of $R^{35}$ is preferably a group in which 50% or more of the hydrogen atoms in the alkyl group are fluorinated, more preferably a group in which 70% or more of the hydrogen atoms in the alkyl group are fluorinated, and still more preferably a group in which 90% or more of the hydrogen atoms in the alkyl group are fluorinated, because the strength of the generated acid increases. The fluorinated alkyl group of $R^{35}$ is most preferably a completely fluorinated alkyl group in which 100% of the hydrogen atoms are substituted with fluorine atoms.

In the general formula (B-3), the alkyl group containing no substituent group or the halogenated alkyl group of $R^{36}$ represents the same as those described above in the alkyl group containing no substituent group or the halogenated alkyl group of $R^{33}$.

Examples of the bivalent or trivalent aromatic hydrocarbon group of $R^{37}$ include aryl groups of $R^{34}$ in which one or two hydrogen atoms are further removed.

The alkyl group containing no substituent group or the halogenated alkyl group of $R^{38}$ represents the same as those described above in the alkyl group containing no substituent group or the halogenated alkyl group of $R^{35}$.

p" is preferably 2.

Specific examples of the oxime sulfonate-based acid generator include
a-(p-toluenesulfonyloxyimino)-benzylcyanide,
a-(p-chlorobenzenesulfonyloxyimino)-benzylcyanide,
a-(4-nitrobenzenesulfonyloxyimino)-benzylcyanide,
a-(4-nitro-2-trifluoromethylbenzenesulfonyloxyimino)-benzylcyanide,
a-(benzenesulfonyloxyimino)-4-chlorobenzylcyanide,
a-(benzenesulfonyloxyimino)-2,4-dichlorobenzylcyanide,
a-(benzenesulfonyloxyimino)-2,6-dichlorobenzylcyanide,
a-(benzenesulfonyloxyimino)-4-methoxybenzylcyanide,
a-(2-chlorobenzenesulfonyloxyimino)-4-methoxybenzylcyanide,
a-(benzenesulfonyloxyimino)-thien-2-ylacetonitrile,
a-(4-dodecylbenzenesulfonyloxyimino)-benzylcyanide,
a-[(p-toluenesulfonyloxyimino)-4-methoxyphenyl]acetonitrile,
a-[(dodecylbenzenesulfonyloxyimino)-4-methoxyphenyl]acetonitrile,
a-(tosyloxyimino)-4-thienylcyanide,
a-(methylsulfonyloxyimino)-1-cyclopentenylacetonitrile,
a-(methylsulfonyloxyimino)-1-cyclohexenylacetonitrile,
a-(methylsulfonyloxyimino)-1-cycloheptenylacetonitrile,
a-(methylsulfonyloxyimino)-1-cyclooctenylacetonitrile,
a-(trifluoromethylsulfonyloxyimino)-1-cyclopentenylacetonitrile,
a-(trifluoromethylsulfonyloxyimino)-cyclohexylacetonitrile,
a-(ethylsulfonyloxyimino)-ethylacetonitrile,
a-(propylsulfonyloxyimino)-propylacetonitlile,
a-(cyclohexylsulfonyloxyimino)-cyclopentylacetonitrile,
a-(cyclohexylsulfonyloxyimino)-cyclohexylacetonitrile,
a-(cyclohexylsulfonyloxyimino)-1-cyclopentenylacetonitrile,
a-(ethylsulfonyloxyimino)-1-cyclopentenylacetonitrile,
a-(isopropylsulfonyloxyimino)-1-cyclopentenylacetonitrile,
a-(n-butylsulfonyloxyimino)-1-cyclopentenylacetonitrile,
a-(ethylsulfonyloxyimino)-1-cyclohexenylacetonitrile,
a-(isopropylsulfonyloxyimino)-1-cyclohexenylacetonitrile,
a-(n-butylsulfonyloxyimino)-1-cyclohexenylacetonitrile,
a-(methylsulfonyloxyimino)-phenylacetonitrile,
a-(methylsulfonyloxyimino)-p-methoxyphenylacetonitrile,
a-(trifluoromethylsulfonyloxyimino)-phenylacetonitrile,
a-(trifluoromethylsulfonyloxyimino)-p-methoxyphenylacetonitrile,
a-(ethylsulfonyloxyimino)-p-methoxyphenylacetonitrile,
a-(propylsulfonyloxyimino)-p-methylphenylacetonitrile, and
a-(methylsulfonyloxyimino)-p-bromophenylacetonitrile.

Also, oxime sulfonate-based acid generators disclosed in Japanese Unexamined Patent Application, First Publication No. Hei9-208554 ([Formula 18] and [Formula 19] in paragraphs [0012] to [0014]), and International Publication WO 2004/074242A2 (Examples 1 to 40 on pages 65 to 85) can be preferably used.

Further, suitable examples thereof include the following.

[Chemical Formula 39]

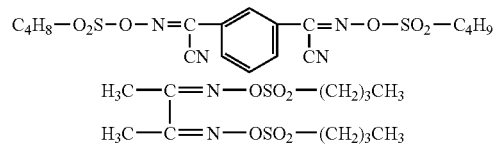

[Chemical Formula 40]

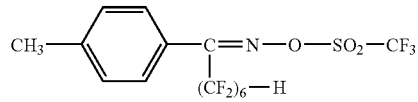

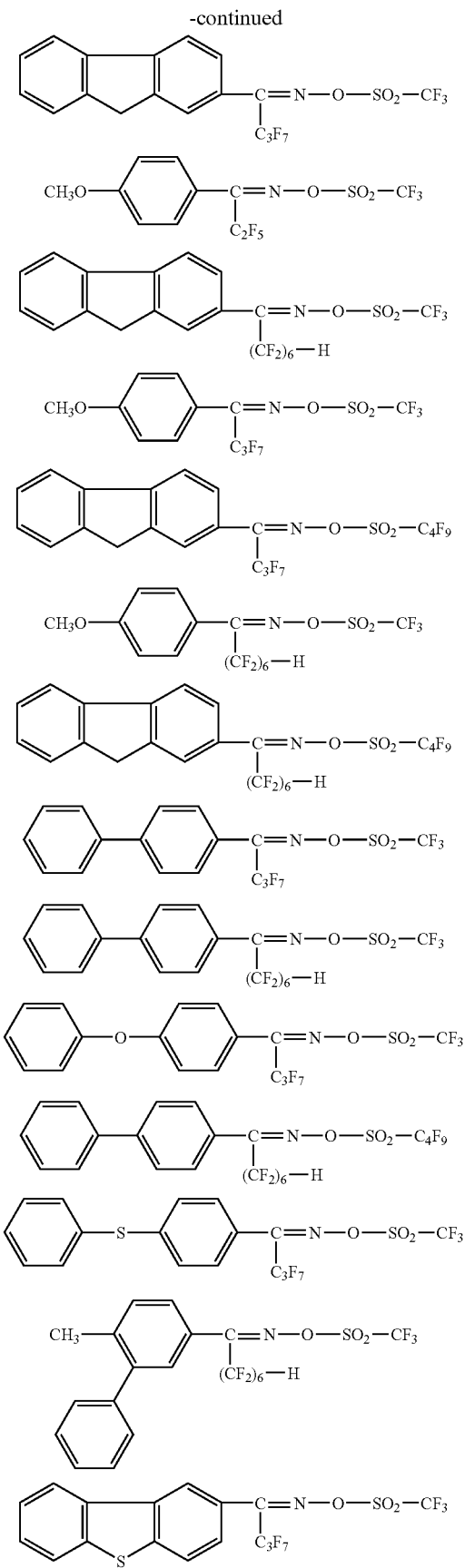

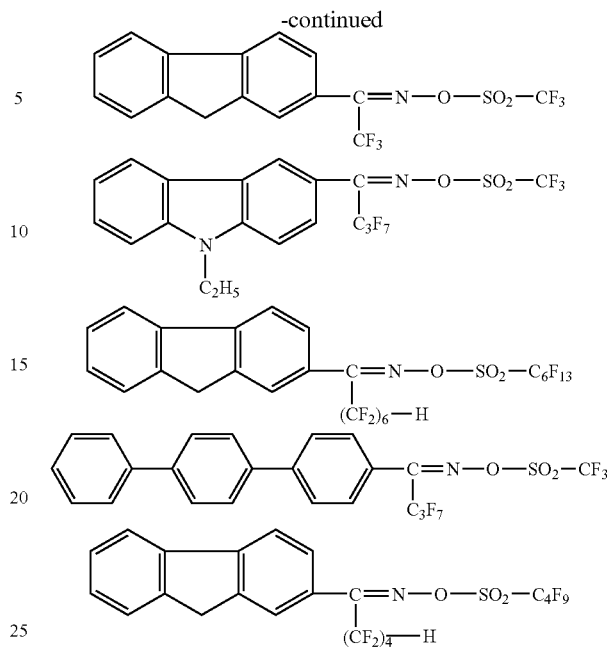

Of these compounds, the four compounds shown below are preferable.

[Chemical Formula 41]

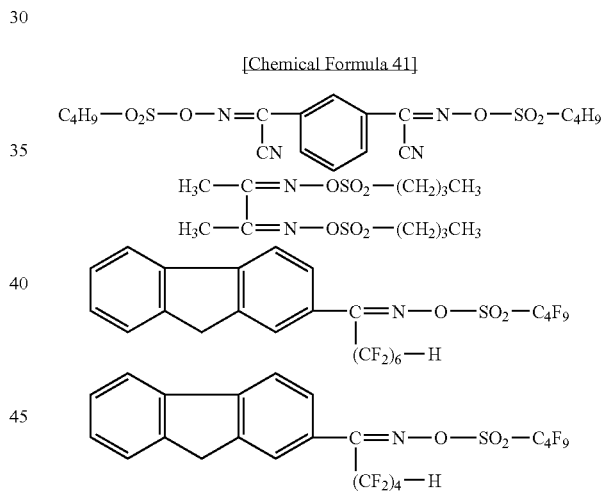

Among the diazomethane-based acid generators, specific examples of bisalkyl- or bisarylsulfonyldiazomethanes include bis(isopropylsulfonyl)diazomethane, bis(p-toluenesulfonyldiazomethane, bis(1,1-dimethylethylsulfonyl)diazomethane, bis(cyclohexylsulfonyl)diazomethane, and bis(2,4-dimethylphenylsulfonyl)diazomethane.

Also, diazomethane-based acid generators disclosed in Japanese Unexamined Patent Application, First Publication No. Hei11-035551, Japanese Unexamined Patent Application, First Publication No. Hei11-035552, and Japanese Unexamined Patent Application, First Publication No. Hei11-035573 can be preferably used. Examples of the poly(bissulfonyl)diazomethanes include
1,3-bis(phenylsulfonyldiazomethylsulfonyl)propane,
1,4-bis(phenylsulfonyldiazomethylsulfonyl)butane,
1,6-bis(phenylsulfonyldiazomethylsulfonyl)hexane,
1,10-bis(phenylsulfonyldiazomethylsulfonyl)decane,
1,2-bis(cyclohexylsulfonyldiazomethylsulfonyl)ethane, 1,3-bis(cyclohexylsulfonyldiazomethylsulfonyl)propane, 1,6-bis(cyclohexylsulfonyldiazomethylsulfonyl)hexane, and 1,10-bis(cyclohexylsulfonyldiazomethylsulfonyl)decane, which are disclosed in Japanese Unexamined Patent Application, First Publication No. Hei11-322707.

As the component (B3), one of the above acid generators may be used alone, or two or more of them may be used in combination.

The amount of the component (B) in the resist composition of the present invention is preferably within a range from 0.5 to 30 parts by mass, and more preferably from 1 to 20 parts by mass, relative to 100 parts by mass of the component (A). When the amount is within the range, a pattern can be sufficiently formed. Also, a uniform solution and an excellent storage stability can be obtained, therefore an amount within the range is preferable.

Component (D)

In the resist composition of the present invention, for improving the resist pattern shape and the post exposure stability of the latent image formed by the pattern-wise exposure of the resist layer, it is preferable to add a nitrogen-containing organic compound (D) (hereafter, referred to as component (D)) as an optional component.

Since a multitude of these components (D) have already been proposed, any of these known compounds can be arbitrarily used. Of these, an aliphatic amine, particularly a secondary aliphatic amine or tertiary aliphatic amine is preferred. Here, in the present claims and specification, the term "aliphatic" is a relative concept used in relation to the term "aromatic", and defines a group or compound or the like that contains no aromaticity.

The term "aliphatic cyclic group (alicyclic group)" represents a monocyclic or polycyclic group that contains no aromaticity. An aliphatic amine is an amine having one or more aliphatic groups, and the aliphatic groups preferably have 1 to 12 carbon atoms.

Examples of the aliphatic amine include an amine (alkylamine or alkylalcoholamine) wherein at least one of the hydrogen atoms of $NH_3$ is substituted with an alkyl or hydroxyalkyl group having 12 or less carbon atoms.

Specific examples of the alkylamines or alkylalcoholamines include monoalkylamines such as n-hexylamine, n-heptylamine, n-octylamine, n-nonylamine, or n-decylamine; dialkylamines such as diethylamine, di-n-propylamine, di-n-heptylamine, di-n-octylamine, or dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine, or tri-n-dodecylamine; and alkylalcoholamines such as diethanolamine, triethanolamine, diisopropanolamine, triisopropanolamine, di-n-octanolamine, or tri-n-octanolamine. Among these amines, trialkylamines of 5 to 10 carbon atoms are preferable, tri-n-pentylamine and tri-n-octylamine are more preferable, and tri-n-pentylamine is most preferable.

Examples of the cyclic amine include a heterocyclic compound containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amines include piperidine, and piperazine.

The aliphatic polycyclic amine preferably has 6 to 10 carbon atoms, and specific examples thereof include 1,5-diazabicyclo[4.3.0]-5-nonene, 1,8-diazabicyclo [5.4.0]-7-undecene, hexamethylenetetramine, and 1,4-diazabicyclo [2.2.2]octane.

These may be used either alone, or in combination of two or more different compounds.

The component (D) is typically used in a quantity within a range from 0.01 to 5.0 parts by weight, relative to 100 parts by weight of the component (A).

Optional Component (Component (E))

In the positive resist composition of the present invention, in order to prevent any deterioration in sensitivity, and improve the resist pattern shape and the post exposure stability of the latent image formed by the pattern-wise exposure of the resist layer, at least one compound (E) selected from the group consisting of organic carboxylic acids and phosphorus oxo acids or derivatives thereof (hereinafter, referred to as component (E)) can also be added as an optional component.

Suitable examples of organic carboxylic acids include acetic acid, malonic acid, citric acid, malic acid, succinic acid, benzoic acid, and salicylic acid.

Examples of phosphorus oxo acids or derivatives thereof include phosphoric acid, phosphonic acid and phosphinic acid. Among these, phosphonic acid is particularly preferable.

Examples of phosphorus oxo acid derivatives include esters in which a hydrogen atom within the above-mentioned oxo acids is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphate esters such as di-n-butyl phosphate and diphenyl phosphate.

Examples of phosphonic acid derivatives include phosphonate esters such as dimethyl phosphonate, di-n-butyl phosphonate, phenylphosphonic acid, diphenyl phosphonate and dibenzyl phosphonate.

Examples of phosphinic acid derivatives include phosphinic esters such as phenylphosphinic acid.

As the component (E), one type may be used alone, or two or more types may be used in combination.

As the component (E), an organic carboxylic acid is preferable, and salicylic acid is particularly preferable.

The component (E) is used in a quantity within a range from 0.01 to 5.0 parts by weight, relative to 100 parts by weight of the component (A).

In the positive resist composition of the present invention, if desired, additives having miscibility, for example, additive resins for improving performance of a resist film, surfactants for improving coatability, dissolution inhibitors, plasticizers, stabilizers, colorants, antihalation agents, and dyes can be appropriately added.

Component (S)

The resist composition of the present invention can be prepared by dissolving materials in an organic solvent (hereinafter, sometimes referred to as component (S)). The component (S) may be an organic solvent which can dissolve the respective components used in the present invention to give a uniform solution, and one or more kinds of organic solvents can be used, appropriately selected from those which have been conventionally known as a solvent for a chemically-amplified resist.

Examples thereof include lactones such as ?-butyrolactone; ketones such as acetone, methyl ethyl ketone, cyclohexanone, methyl-n-pentyl ketone, methyl isopentyl ketone, and 2-heptanone; polyhydric alcohols such as ethylene glycol, diethylene glycol, propylene glycol, dipropylene glycol;

derivatives of the polyhydric alcohols, including compounds having ester bonds such as ethylene glycol monoacetate, diethylene glycol monoacetate, propylene glycol monoacetate and dipropylene glycol monoacetate, and compounds having ether bonds such as monoalkyl ethers (for example, monomethyl ether, monoethyl ether, monopropyl ether and monobutyl ether) and monophenyl ether of the above polyhydric alcohols or the above compounds having ester bonds (of these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, ethyl ethoxypropionate; and aromatic organic solvents such as anisole, ethylbenzyl ether, cresylmethyl ether, diphenyl ether, dibenzyl ether, phenetol, butylphenyl ether, ethylbenzene, diethylbenzene, pentylbenzene, isopropylbenzene, toluene, xylene, cymene, and mesitylene.

These organic solvents may be used either alone, or as a mixed solvent of two or more different solvents.

Of these, propylene glycol monomethyl ether acetate (PGMEA), propylene glycol monomethyl ether (PGME), ethyl lactate (EL) and ?-butyrolactone are preferable.

Also, a mixed solvent obtained by mixing PGMEA and a polar solvent is preferable. The mixing ratio (mass ratio) of PGMEA to the polar solvent may be appropriately decided taking account of compatibility, and is preferably adjusted within a range from 1:9 to 9:1, and more preferably from 2:8 to 8:2.

More specifically, in the case of using EL as the polar solvent, the mass ratio PGMEA:EL is preferably from 1:9 to 9:1, and more preferably from 2:8 to 8:2. Furthermore, in those cases of using PGME as the polar solvent, the mass ratio PGME:PGME is preferably from 1:9 to 9:1, more preferably 2:8 to 8:2, and still more preferably 3:7 to 7:3.

Furthermore, as the component (S), mixed solvents of at least one of PGMEA and EL with ?-butyrolactone are also preferred. In such cases, the mass ratio of the former and latter components in the mixed solvents is preferably within a range from 70:30 to 95:5.

Furthermore, as the component (S), a mixed solvent of a mixture of PGMEA and PGME with ?-butyrolactone is also preferable. The mixing ratio (former: latter) of such a mixed solvent is preferably from 99.9:0.1 to 80:20, more preferably from 99.9:0.1 to 90:10, and most preferably from 99:9:0.1 to 95:5.

By virtue of the above-mentioned range, the rectangularity of the resist pattern is improved.

There is no particular restriction on the quantity of the component (S), and the quantity should be set in accordance with the required coating film thickness within a concentration that enables favorable application of the solution to a substrate or the like. Typically, the quantity is set so that the solid fraction concentration within the resist composition falls within a range from 2 to 20% by weight, and still more preferably from 5 to 15% by weight.

In the resist composition of the present invention, the components (B1) and (B2) are used as the acid generator. The components (B1) and (B2) have excellent solubility in an organic solvent (resist solvent) used to dissolve resist components, as compared to acid generators having triphenylsulfonium (TPS) or the like as the cation moiety. Further, they are advantageous in that photoabsorption is effectively suppressed in the exposure wavelength range (especially, wavelength range for ArF excimer laser), and they exhibit high transparency, and hence, they can be used in large amounts in the resist composition. As a result, it is presumed that the concentration of the acid generator within the resist film can be increased, and efficiency of acid generation can be enhanced. Also, since they have high solubility in the resist solvents, it is presumed that the components can be more uniformly dispersed within the resist film than conventional acid generators. It is also presumed that the above efficiency can be further enhanced by using the components (B1) and (B2), whose anion moieties have different skeletons, in combination.

For these reasons described above, it is presumed that, in the resist composition of the present invention, by using a base component in combination with an acid generator (the components (B1) and (B2)), footing on the interface between the resist film and the substrate is suppressed, and the resist pattern thus obtained has excellent verticality and excellent rectangularity even on an inorganic anti-reflection film (inorganic BARC) or an organic anti-reflection film (organic BARC). Further, it is also presumed that, since the components (B1) and (B2) have excellent solubility in the resist solvents, they enhance storage stability of the resist, thereby enabling a resist pattern with excellent lithography properties to be formed. Furthermore, the resist composition of the present invention can be preferably used as a resist composition for an immersion lithography in a method of forming a resist pattern which includes the step of conducting immersion lithography, and also can exhibit excellent lithography properties. Also, the present composition of the present invention can be preferably used as a resist composition for forming an upper-layer resist film in a method of forming a resist pattern which includes the step of forming a three-layered resist laminate, and also can exhibit excellent lithography properties.

<<Method of Forming Resist Pattern >>

Next, a method of forming a resist pattern according to the second embodiment of the present invention will be described below.

The method of forming a resist pattern of the present invention includes applying a resist composition described in the first aspect of the present invention to a substrate to form a resist film on the substrate; conducting exposure of the resist film; and alkali-developing the resist film to form a resist pattern.

The method of forming a resist pattern of the present invention can be performed, for example, in the following manner.

Namely, the resist composition described in the first embodiment of the present invention is first applied to a substrate using a spinner or the like, a prebake (post applied bake (PAB)) is then conducted under temperature conditions of 80 to 150° C. for 40 to 120 seconds, preferably for 60 to 90 seconds, followed by selective exposure of the thus obtained film with an ArF exposure apparatus or the like, by irradiating ArF excimer laser light through a desired mask pattern, and then PEB (post exposure baking) is conducted under temperature conditions of 80 to 150° C. for 40 to 120 seconds, preferably for 60 to 90 seconds. Subsequently, a developing treatment is conducted using an alkali developing solution such as a 0.1 to 10% by mass aqueous solution of tetramethylammonium hydroxide, preferably followed by rinsing with pure water, and drying. In this manner, a resist pattern that is faithful to the mask pattern can be obtained.

The substrate is not specifically limited and a conventionally known substrate can be used. For example, substrates for electronic components, and such substrates having prescribed wiring patterns formed thereon can be exemplified. Specific examples thereof include substrates made of metals such as silicon wafer, copper, chromium, iron and aluminum; and substrates made of glass. As materials for the wiring pattern, for example, copper, aluminum, nickel and gold can be used.

Further, as the substrate, any one of the above-exemplified substrates provided with an inorganic and/or organic film on the surface thereof may be used. As the inorganic film, an inorganic anti-reflection film (inorganic BARC) can be exemplified. As the organic film, an organic anti-reflection film (organic BARC) can be exemplified.

There is no particular restriction on the wavelength used for the exposure, and the exposure can be conducted using radiation such as ArF excimer lasers, KrF excimer lasers, $F_2$ excimer lasers, extreme ultraviolet rays (EUV), vacuum ultraviolet rays (VUV), electron beams (EB), X-rays, and soft X-rays. The resist composition of the present invention is effective when radiation from KrF excimer lasers, ArF excimer lasers, EB and EUV is irradiated, and particularly effective when radiation from ArF excimer lasers is irradiated.

EXAMPLES

The following is a description of examples of the present invention, although the scope of the present invention is by no way limited by these examples.

Examples 1 to 11 and Comparative Examples 1 and 2

Preparation of Positive Resist Composition

The components shown in Table 1 are mixed and dissolved, thereby providing a positive resist composition.

(A)-2: a polymer represented by a general formula (A)-2 shown below (Mw=5,000; Mw/Mn=1.8).

(A)-3: a polymer represented by a general formula (A)-3 shown below (Mw=5,000; Mw/Mn=1.8).

(A)-4: a polymer represented by a general formula (A)-4 shown below (Mw=5,000; Mw/Mn=1.8).

(A)-5: a polymer represented by a general formula (A)-5 shown below (Mw=5,000; Mw/Mn=1.8).

(A)-6: a polymer represented by a general formula (A)-6 shown below (Mw=5,000; Mw/Mn=1.8).

(A)-7: a polymer represented by a general formula (A)-7 shown below (Mw=5,000; Mw/Mn=1.8).

(A)-8: a polymer represented by a general formula (A)-8 shown below (Mw=5,000; Mw/Mn=1.8).

(A)-9: a polymer represented by a general formula (A)-9 shown below (Mw=5,000; Mw/Mn=1.8).

(A)-10: a polymer represented by a general formula (A)-10 shown below (Mw=5,000; Mw/Mn=1.8).

(A)-11: a polymer of 2-methacryloyloxy-2-methyladamantane/a-methacryloyloxy-?-butyrolactone/1-methacryloyloxy-3-hydroxyadamantane=4/4/2 (molar ratio)(Mw=7,000; Mw/Mn=1.8).

(B)-1: an acid generator represented by a general formula (b1-6-11 shown below.

(B)-2: an acid generator represented by a general formula (b1-6-23) shown below.

(B)-3: an acid generator represented by a general formula (B)-3 shown below.

(B)-4: an acid generator represented by a general formula (B)-4 shown below.

(B)-5: an acid generator represented by a general formula (B)-5 shown below.

TABLE 1

|  | Component (A) | | Component (B) | | Component (D) | Component (E) | Component (S) | |
| --- | --- | --- | --- | --- | --- | --- | --- | --- |
| Example 1 | (A)-1 [50] | (A)-2 [50] | (B)-1 [5.0] | (B)-2 [9.0] | (D)-1 [0.55] | (E)-1 [1.32] | (S)-1 [2000] | (S)-2 [10] |
| Example 2 | (A)-1 [50] | (A)-2 [50] | (B)-1 [6.5] | (B)-2 [6.5] | (D)-1 [0.55] | (E)-1 [1.32] | (S)-1 [2000] | (S)-2 [10] |
| Example 3 | (A)-1 [50] | (A)-3 [50] | (B)-1 [6.5] | (B)-2 [6.5] | (D)-1 [0.55] | (E)-1 [1.32] | (S)-1 [2000] | (S)-2 [10] |
| Example 4 | (A)-1 [50] | (A)-4 [50] | (B)-1 [6.5] | (B)-2 [6.5] | (D)-1 [0.55] | (E)-1 [1.32] | (S)-1 [2000] | (S)-2 [10] |
| Example 5 | (A)-1 [50] | (A)-5 [50] | (B)-1 [6.5] | (B)-2 [6.5] | (D)-1 [0.55] | (E)-1 [1.32] | (S)-1 [2000] | (S)-2 [10] |
| Example 6 | (A)-3 [100] | | (B)-1 [6.5] | (B)-2 [6.5] | (D)-1 [0.55] | (E)-1 [1.32] | (S)-1 [2000] | (S)-2 [10] |
| Example 7 | (A)-1 [50] | (A)-6 [50] | (B)-1 [6.5] | (B)-2 [6.5] | (D)-1 [0.55] | (E)-1 [1.32] | (S)-1 [2000] | (S)-2 [10] |
| Example 8 | (A)-1 [50] | (A)-7 [50] | (B)-1 [6.5] | (B)-2 [6.5] | (D)-1 [0.55] | (E)-1 [1.32] | (S)-1 [2000] | (S)-2 [10] |
| Example 9 | (A)-1 [50] | (A)-8 [50] | (B)-1 [6.5] | (B)-2 [6.5] | (D)-1 [0.55] | (E)-1 [1.32] | (S)-1 [2000] | (S)-2 [10] |
| Example 10 | (A)-1 [50] | (A)-9 [50] | (B)-1 [6.5] | (B)-2 [6.5] | (D)-1 [0.55] | (E)-1 [1.32] | (S)-1 [2000] | (S)-2 [10] |
| Example 11 | (A)-1 [50] | (A)-10 [50] | (B)-1 [6.5] | (B)-2 [6.5] | (D)-1 [0.55] | (E)-1 [1.32] | (S)-1 [2000] | (S)-2 [10] |
| Comparative Example 1 | (A)-11 [100] | | (B)-3 [3.0] | (B)-4 [6.0] | (D)-1 [0.50] | (E)-1 [1.32] | (S)-1 [2000] | (S)-2 [10] |
| Comparative Example 2 | (A)-11 [100] | | (B)-4 [6.0] | (B)-5 [4.5] | (D)-1 [0.41] | (E)-1 [1.32] | (S)-1 [2000] | (S)-2 [10] |

In Table 1, the abbreviations represent the following meanings. Also, values within the brackets [ ] represent the amount (parts by weight) of the components added in the resist composition.

(A)-1: a polymer represented by a general formula (A)-1 shown below (Mw=5,000; Mw/Mn=1.8).

(D)-1: tri-n-pentylamine.

(E)-1: salicylic acid.

(S)-1: a mixture solvent of PGMEA/PGME=6/4 (mass ratio).

(S)-2: ?-butyrolactone.

[Chemical Formula 42]
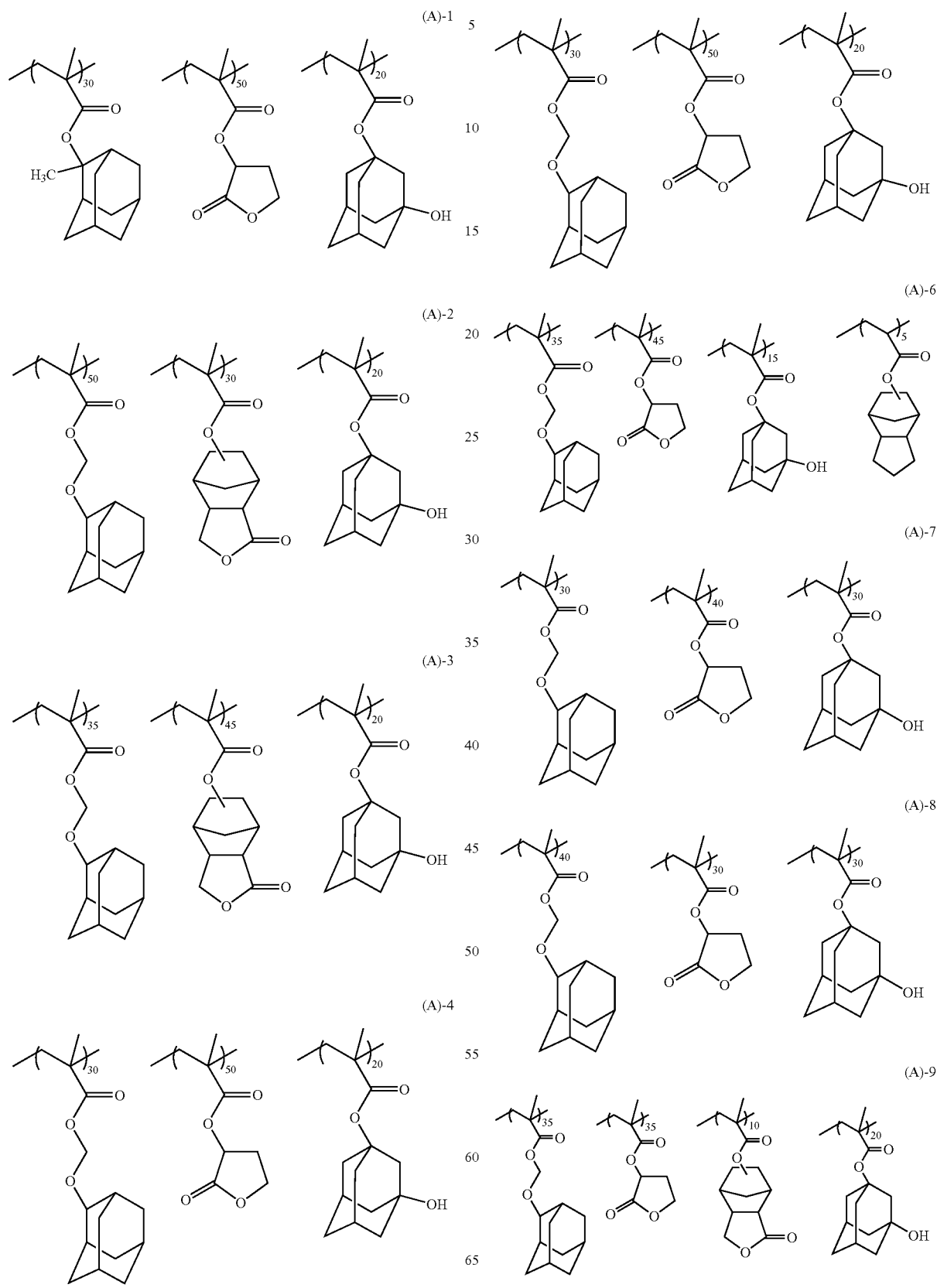

-continued (A)-10

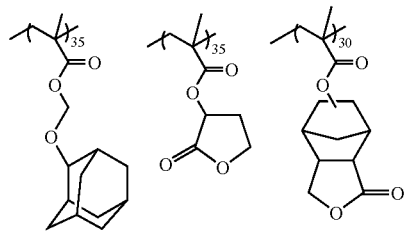

[Chemical Formula 43]

(b1-6-11)

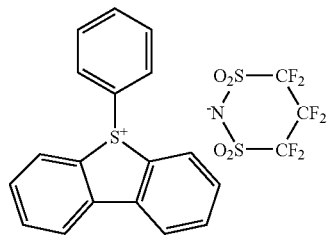

(b1-6-23)

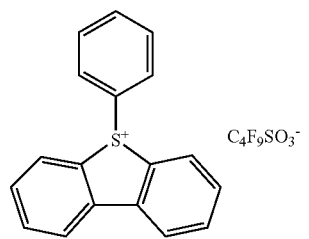

(B)-3

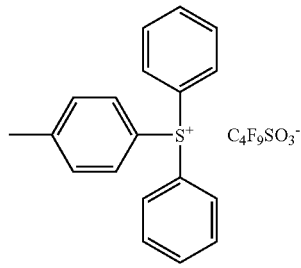

(B)-4

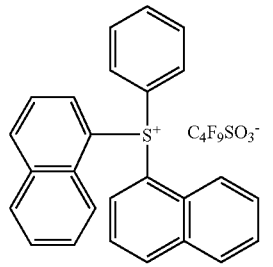

-continued (B)-5

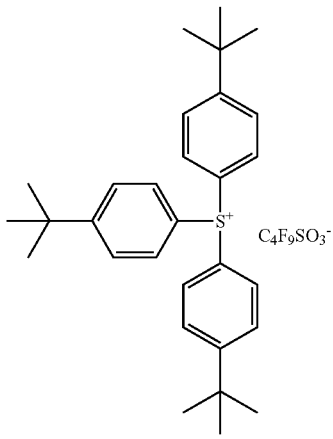

The polymers (A)-1 to (A)-8 were synthesized by a conventional dropwise polymerization method using monomers which derive the respective structural units. In the formula (A)-1, the subscript numerals on the brackets indicate the percentage (mol %) of the respective structural units within the copolymer. The composition ratio was determined by $^{13}$C-NMR. Further, Mw and Mw/Mn were determined by the polystyrene equivalent value as measured by gel permeation chromatography (GPC).

<Evaluation of Lithography Properties>

Resist patterns were formed using the positive resist composition solutions thus obtained, and the following lithography properties were evaluated.

[Resolution and Sensitivity]

An organic anti-reflection film composition (product name: ARC-95, manufactured by Brewer Science Ltd.) was applied onto an 8-inch silicon wafer using a spinner, and the composition was then baked at 190° C. for 60 seconds, thereby forming an organic anti-reflection film having a film thickness of 86 mm. Then, the positive resist composition solution obtained above was applied onto the anti-reflection film using a spinner, and was then prebaked (PAB) on a hotplate at 110° C. for 60 seconds and dried, thereby forming a resist film having a film thickness of 140 nm.

Subsequently, the obtained resist film was selectively exposed by an ArF excimer laser (193 nm), using an ArF exposure apparatus "NSR-S306" (manufactured by Nikon; numerical aperture (NA) 0.78, Dipole Y) through a mask pattern. Thereafter, a post exposure bake (PEB) treatment was conducted at 110° C. for 60 seconds, followed by development for 30 seconds at 23° C. in a 2.38% by weight aqueous solution of tetramethylammonium hydroxide (TMAH). Then, the resist was washed for 30 seconds with pure water, followed by drying by shaking, thereby forming a resist pattern (L/S pattern) with a line and space (1:1). The optimum exposure dose (sensitivity. Eop, mJ/cm$^2$) for forming the L/S pattern with a line width of 90 nm and a pitch of 198 nm was determined. The results are shown in Table 2.

TABLE 2

|  | Example 1 | Example 2 | Example 3 | Example 4 | Example 5 | Example 6 |
|---|---|---|---|---|---|---|
| Eop (mJ/cm$^2$) | 48.67 | 57.13 | 45.85 | 48.67 | 38.85 | 36.24 |

|  | Example 7 | Example 8 | Example 9 | Example 10 | Example 11 |
|---|---|---|---|---|---|
| Eop (mJ/cm$^2$) | 42.72 | 52.09 | 45.91 | 46.65 | 47.89 |

|  | Comparative Example 1 | Comparative Example 2 |
|---|---|---|
| Eop (mJ/cm$^2$) | 35.56 | 39.35 |

[Pattern Shape]

The sectional shapes of the resist pattern were observed by a scanning electron microscope (product name: S-4700, manufactured by Hitachi, Ltd.), and it was found that, even in the case that the organic anti-reflecting films were formed on the substrate, footing was suppressed in Examples 1 to 11. Consequently, the resist patterns in Examples 1 to 11 have excellent verticality and excellent rectangularity On the other hand, footing was observed in the resist patterns in Comparative Examples 1 and 2 between the organic anti-reflecting film and the resist film, and the resist patterns were in footing shapes.

From these results, it is confirmed that the resist composition of the present invention can attain excellent lithography properties.

What is claimed is:

1. A resist composition, which comprises a base component (A) which exhibits changed solubility in an alkali developing solution under action of an acid, and an acid generator component (B) which generates an acid upon exposure, wherein the acid generator component (B) comprises an acid generator (B1) represented by a general formula (b1-6-1) shown below and an acid generator (B2) represented by a general formula (b1-6-2) shown below.

[Chemical Formula 1]

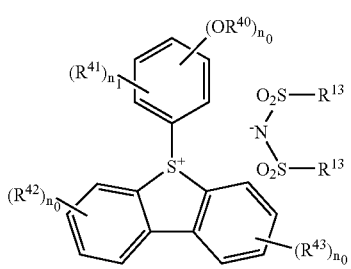

(b1-6-1)

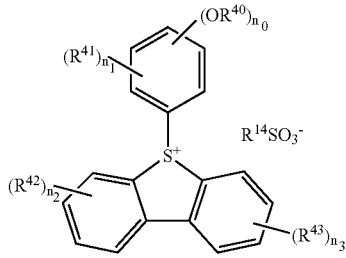

(b1-6-2)

(wherein, $R^{40}$ represents a hydrogen atom or an alkyl group; $R^{41}$ represents a halogen atom, a halogenated alkyl group, an alkyl group, an acetyl group, a carboxyl group or a hydroxyalkyl group; $R^{42}$ and $R^{43}$ each independently represents a halogen atom, a halogenated alkyl group, an alkyl group, an acetyl group, an alkoxy group, a carboxyl group or a hydroxyalkyl group; $n_0$ to $n_3$ each independently represents an integer of 0 to 3, with the proviso that $n_0+n_1$ is 5 or less; $R^{13}$ each independently represents a linear or branched alkyl group of 1 to 10 carbon atoms in which at least one hydrogen atom is substituted with a fluorine atom, and two of $R^{13}$ may be bonded mutually to form a ring structure; $R^{14}$ represents a linear, branched or cyclic alkyl group, a linear, branched or cyclic halogenated alkyl group, an aryl group or an alkenyl group, which may contain a substituent group).

2. The resist composition according to claim 1, wherein the acid generator (B1) is an acid generator represented by a general formula (b1-6-10) shown below:

[Chemical Formula 2]

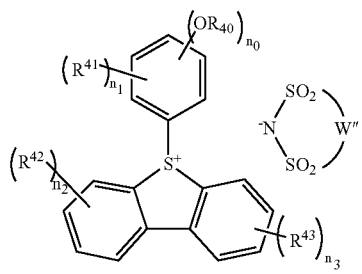

(b1-6-10)

(wherein, $R^{40}$ represents a hydrogen atom or an alkyl group; $R^{41}$ represents a halogen atom, a halogenated alkyl group, an alkyl group, an acetyl group, a carboxyl group or a hydroxyalkyl group; $R^{42}$ and $R^{43}$ each independently represents a halogen atom, a halogenated alkyl group, an alkyl group, an acetyl group, an alkoxy group, a carboxyl group or a hydroxyalkyl group; $n_0$ to $n_3$ each independently represents an integer of 0 to 3, with the proviso that $n_0+n_1$ is 5 or less; and W" represents an alkylene group of 2 to 6 carbon atoms in which all hydrogen atoms are substituted with fluorine atoms).

3. The resist composition according to claim 1, wherein the base component (A) is a base component which exhibits increased solubility in an alkali developing solution under action of acid.

4. The resist composition according to claim 3, wherein the base component (A) is a resin component (A1), and comprises a structural unit (a1) derived from an acrylate ester having an acid dissociable, dissolution inhibiting group.

5. The resist composition according to claim 4, wherein the base component (A) comprises a structural unit (a2) derived from an acrylate ester having a lactone-containing cyclic group.

6. The resist composition according to claim 4, wherein the base component (A) comprises a structural unit (a3) derived from an acrylate ester having a polar group-containing aliphatic hydrocarbon group.

7. The resist composition according to claim 5, wherein the base component (A) comprises a structural unit (a3) derived from an acrylate ester having a polar group-containing aliphatic hydrocarbon group.

8. The resist composition according to claim 1, further comprising a nitrogen-containing organic compound (D).

9. A method of forming a resist pattern, comprising:
forming a resist film on a substrate using the positive resist composition described in any one of claims 1 to 8;
exposing the resist film; and
alkali-developing the resist film to form a resist pattern.

* * * * *

UNITED STATES PATENT AND TRADEMARK OFFICE
CERTIFICATE OF CORRECTION

PATENT NO. : 7,491,485 B2
APPLICATION NO. : 12/124013
DATED : February 17, 2009
INVENTOR(S) : Takeshita et al.

It is certified that error appears in the above-identified patent and that said Letters Patent is hereby corrected as shown below:

Title page (Item 57) Abstract, Line 11 (Approx.), change

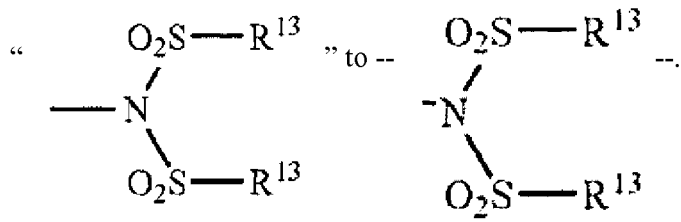

Column 1, Line 22, change "ten" to --then--.

Column 4, Line 64, change "glycoluryl" to --glycoluril--.

Column 24, Line 59, after "[Chemical Formula15]" change "(a1-1-32)" to --(a1-2-32)--.

Column 25, Line 47 (Approx.), change "a1-2-38)" to --(a1-2-38)--.

Column 34, Line 29 (Approx.), change "(aq-4-2)" to --(a1-4-2)--.

Column 42, Lines 5-30 (Approx.), change

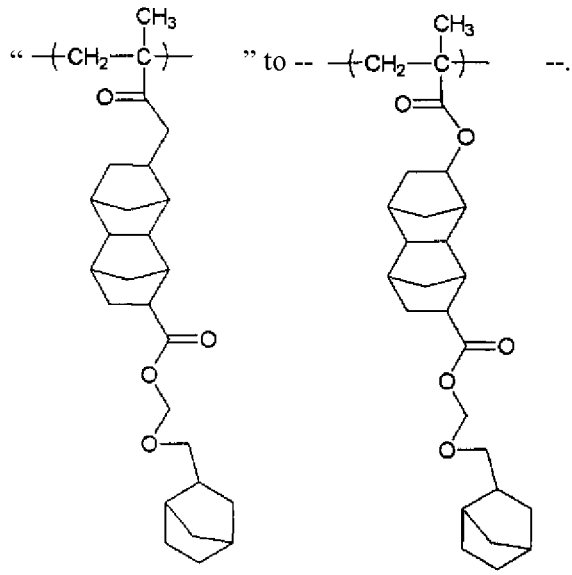

UNITED STATES PATENT AND TRADEMARK OFFICE
CERTIFICATE OF CORRECTION

PATENT NO. : 7,491,485 B2
APPLICATION NO. : 12/124013
DATED : February 17, 2009
INVENTOR(S) : Takeshita et al.

It is certified that error appears in the above-identified patent and that said Letters Patent is hereby corrected as shown below:

Column 51, Line 66, change "11" to --1;--.

Column 69, Line 34, change "–CHCH$_2$CF$_2$–," to -- –CH$_2$CH$_2$CF$_2$–,--.

Column 73, Line 59, change "sane" to --same--.

Column 78, Line 22, change "propylacetonitlile," to --propylacetonitrile,--.

Column 83, Line 16, change "phenetol," to --phenetole,--.

Column 86, Line 24, change "11 shown" to --11) shown--.

Column 89, Lines 5-10 (Approx.), change

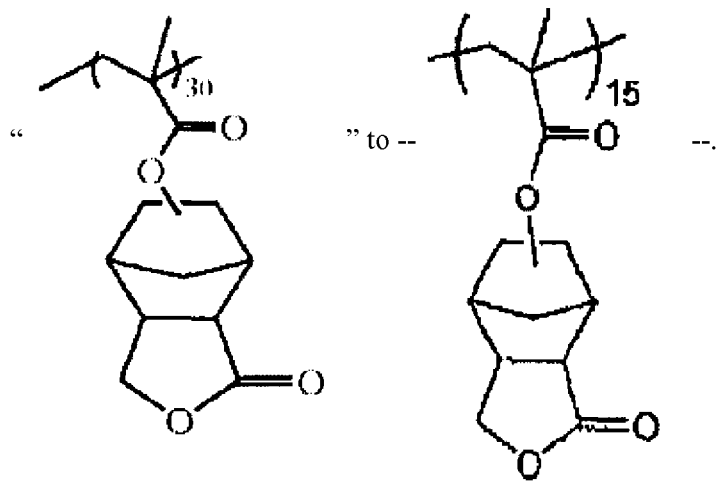

UNITED STATES PATENT AND TRADEMARK OFFICE
CERTIFICATE OF CORRECTION

PATENT NO. : 7,491,485 B2
APPLICATION NO. : 12/124013
DATED : February 17, 2009
INVENTOR(S) : Takeshita et al.

It is certified that error appears in the above-identified patent and that said Letters Patent is hereby corrected as shown below:

Column 90, Line 55 (Approx.), change "(NA) 0.78," to --(NA)=0.78,--.

Column 91, Line 30 (Approx.), change "rectangularity" to --rectangularity.--.

Column 91, Lines 30-35 (Approx.), delete "On the...footing shapes." and insert the same below "rectangularity" on Col. 91, Line 31 (Approx.) as a new paragraph.

Column 91, Line 51, In Claim 1, change "below." to --below:--.

Signed and Sealed this

Seventh Day of July, 2009

JOHN DOLL
*Acting Director of the United States Patent and Trademark Office*